(12) United States Patent
Miller et al.

(10) Patent No.: US 7,513,818 B2
(45) Date of Patent: Apr. 7, 2009

(54) POLISHING ENDPOINT DETECTION SYSTEM AND METHOD USING FRICTION SENSOR

(75) Inventors: Gabriel Lorimer Miller, Eastham, MA (US); Manoocher Birang, Los Gatos, CA (US); Nils Johansson, Los Gatos, CA (US); Boguslaw A. Swedek, Cupertino, CA (US); Dominic J. Benvegnu, La Honda, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/977,479

(22) Filed: Oct. 28, 2004

(65) Prior Publication Data

US 2005/0136800 A1    Jun. 23, 2005

Related U.S. Application Data

(60) Provisional application No. 60/590,471, filed on Jul. 22, 2004, provisional application No. 60/516,349, filed on Oct. 31, 2003.

(51) Int. Cl.
*B24B 49/00* (2006.01)

(52) U.S. Cl. .............................. 451/5; 451/285; 451/28; 451/8

(58) Field of Classification Search ............... 451/5–10, 451/285–288, 41, 28
See application file for complete search history.

(56) References Cited

U.S. PATENT DOCUMENTS

| | | | |
|---|---|---|---|
| 5,036,015 A | 7/1991 | Sandhu et al. | |
| 5,069,002 A | 12/1991 | Sandhu et al. | |
| 5,486,129 A | 1/1996 | Sandhu et al. | |
| 5,597,341 A | 1/1997 | Kodera et al. | |
| 5,623,096 A | 4/1997 | Bandyopadhyay et al. | |
| 5,639,388 A | 6/1997 | Kimura et al. | |
| 5,647,952 A | 7/1997 | Chen | |
| 5,700,180 A | 12/1997 | Sandhu et al. | |
| 5,738,562 A | 4/1998 | Doan et al. | |
| 5,743,784 A | 4/1998 | Birang et al. | |
| 5,830,041 A | 11/1998 | Takahashi et al. | |
| 5,846,882 A | 12/1998 | Birang | |

(Continued)

FOREIGN PATENT DOCUMENTS

CN    1211487    3/1999

(Continued)

OTHER PUBLICATIONS

International Preliminary Report of International Application No. PCT/US2004/036412, mailed May 11, 2006.

*Primary Examiner*—Lee D Wilson
(74) *Attorney, Agent, or Firm*—Fish & Richardson

(57) ABSTRACT

A system, method and apparatus to monitor a frictional coefficient of a substrate undergoing polishing is described. A polishing pad assembly includes a polishing layer including a polishing surface, and a substrate contacting member flexibly coupled to the polishing layer having a top surface to contact an exposed surface of a substrate. At least a portion of the top surface is substantially coplanar with the polishing surface. A sensor is provided to measure a lateral displacement of the substrate contacting member. Some embodiments may provide accurate endpoint detection during chemical mechanical polishing to indicate the exposure of an underlying layer.

24 Claims, 15 Drawing Sheets

U.S. PATENT DOCUMENTS

| | | | |
|---|---|---|---|
| 5,851,135 | A | 12/1998 | Sandhu et al. |
| 5,860,847 | A | 1/1999 | Sakurai et al. |
| 5,914,275 | A | 6/1999 | Kodera et al. |
| 5,948,205 | A | 9/1999 | Kodera et al. |
| 6,046,111 | A | 4/2000 | Robinson |
| 6,120,347 | A | 9/2000 | Sandhu et al. |
| 6,123,609 | A | 9/2000 | Satou |
| 6,191,037 | B1 | 2/2001 | Robinson et al. |
| 6,206,754 | B1 | 3/2001 | Moore |
| 6,257,953 | B1 | 7/2001 | Gitis et al. |
| 6,280,292 | B1 | 8/2001 | Sato et al. |
| 6,283,829 | B1 | 9/2001 | Molnar |
| 6,306,008 | B1 | 10/2001 | Moore |
| 6,340,434 | B1 | 1/2002 | Mizuno et al. |
| 6,428,389 | B2 | 8/2002 | Sato et al. |
| 6,492,273 | B1 | 12/2002 | Hofmann et al. |
| 6,520,834 | B1 | 2/2003 | Marshall |
| 6,572,444 | B1 | 6/2003 | Ball et al. |
| 6,623,334 | B1 | 9/2003 | Birang et al. |
| 6,634,924 | B1 | 10/2003 | Ono et al. |
| 6,699,791 | B2 | 3/2004 | Hofmann et al. |
| 6,711,829 | B2 | 3/2004 | Sano et al. |
| 6,773,332 | B2 * | 8/2004 | Moore ............... 451/5 |
| 6,840,840 | B2 * | 1/2005 | Moore ............... 451/5 |
| 6,916,225 | B2 | 7/2005 | Sugiyama et al. |
| 6,969,297 | B2 * | 11/2005 | Moore ............... 451/5 |
| 7,052,366 | B2 * | 5/2006 | Wolf ................. 451/6 |
| 2001/0008476 | A1 | 7/2001 | Imamura |
| 2001/0012750 | A1 | 8/2001 | Moore |
| 2002/0016131 | A1 | 2/2002 | Sandhu et al. |
| 2002/0037681 | A1 | 3/2002 | Gitis et al. |
| 2002/0090889 | A1 | 7/2002 | Crevasse et al. |
| 2005/0136800 | A1 * | 6/2005 | Miller et al. ......... 451/5 |
| 2006/0003673 | A1 * | 1/2006 | Moore ............... 451/5 |
| 2007/0087662 | A1 * | 4/2007 | Benvegnu et al. ...... 451/5 |

FOREIGN PATENT DOCUMENTS

| | | |
|---|---|---|
| CN | 1425190 A | 6/2003 |
| EP | 0771611 A1 | 7/1997 |
| JP | 2000065720 | 3/2000 |

* cited by examiner

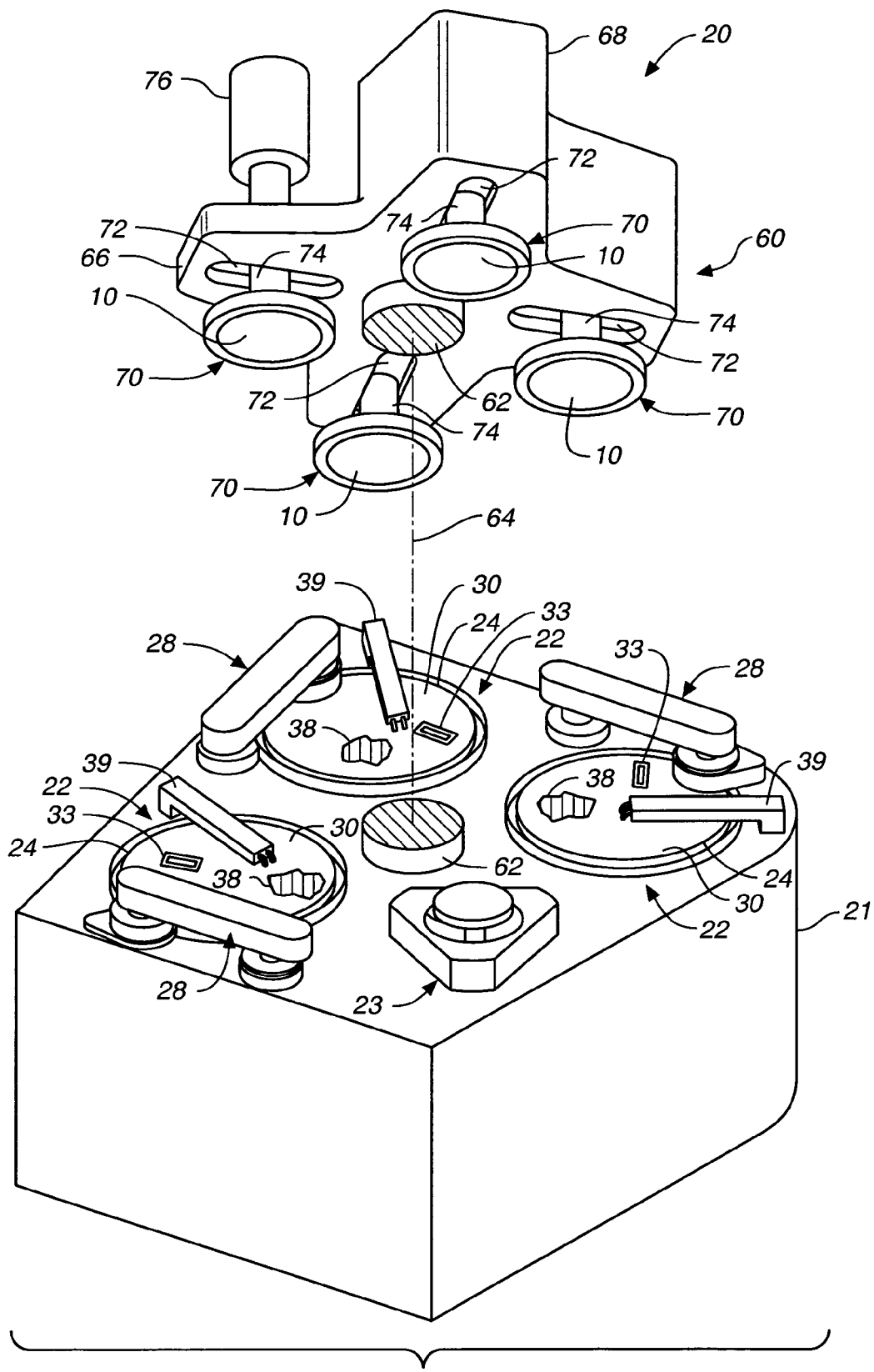
FIG._1

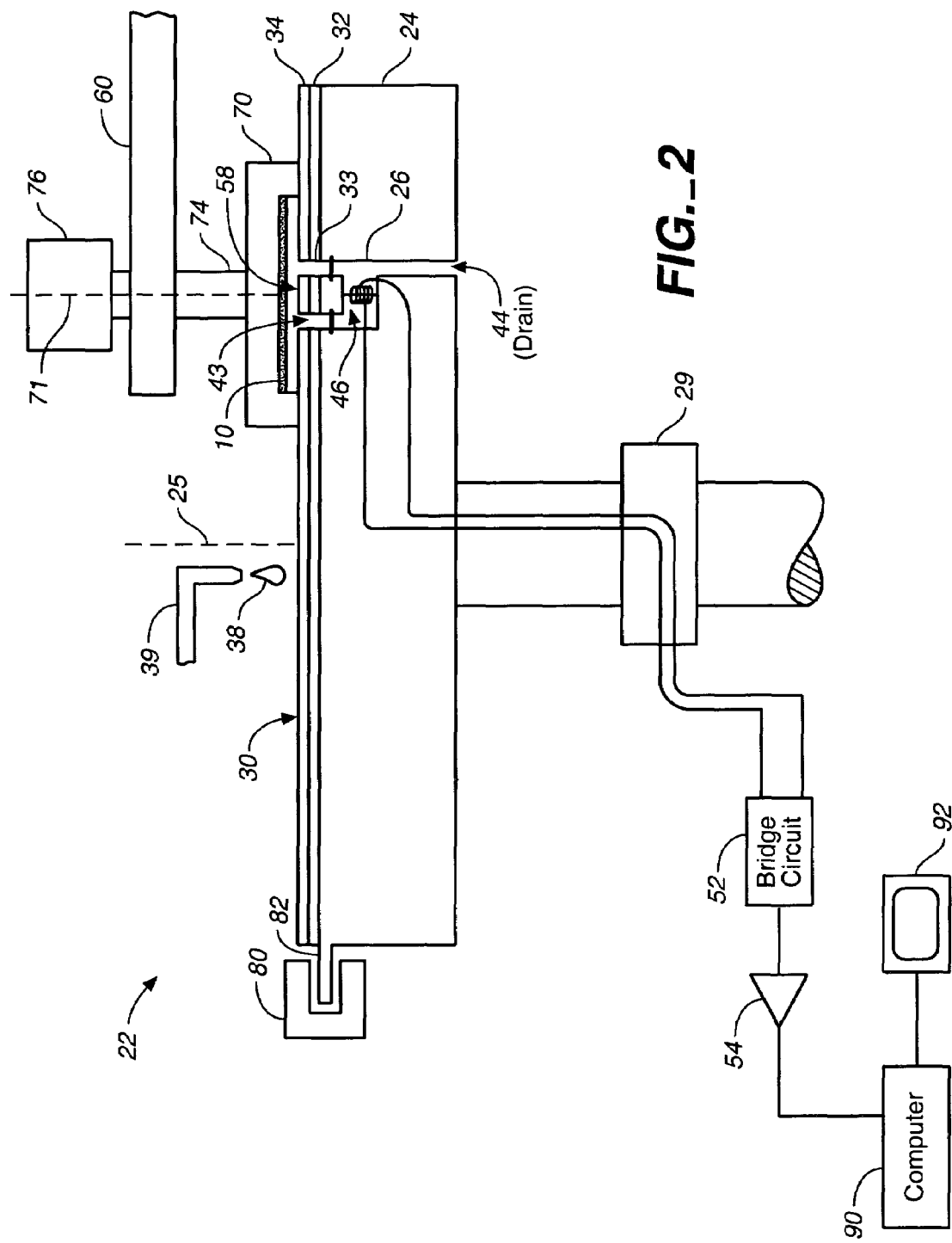
FIG._2

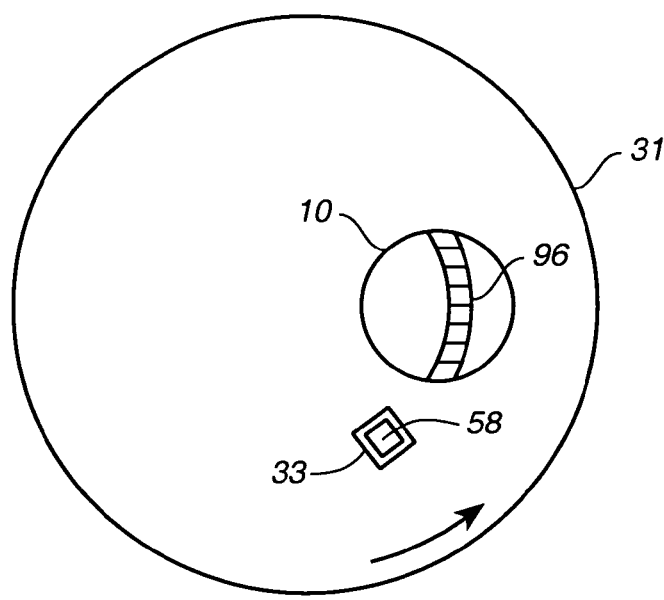
FIG._3
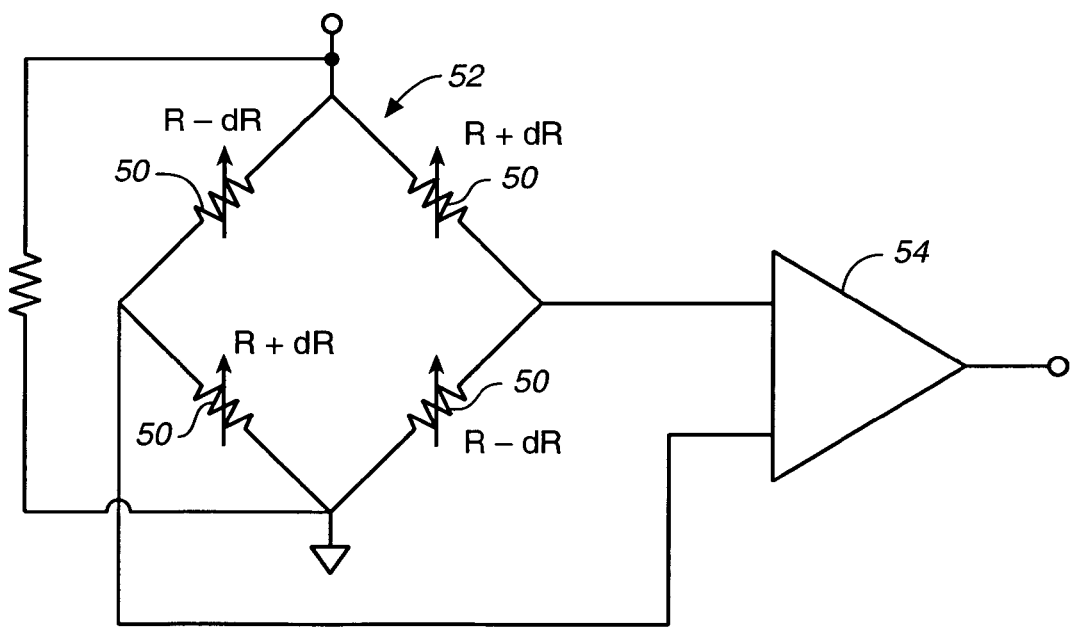
FIG._5

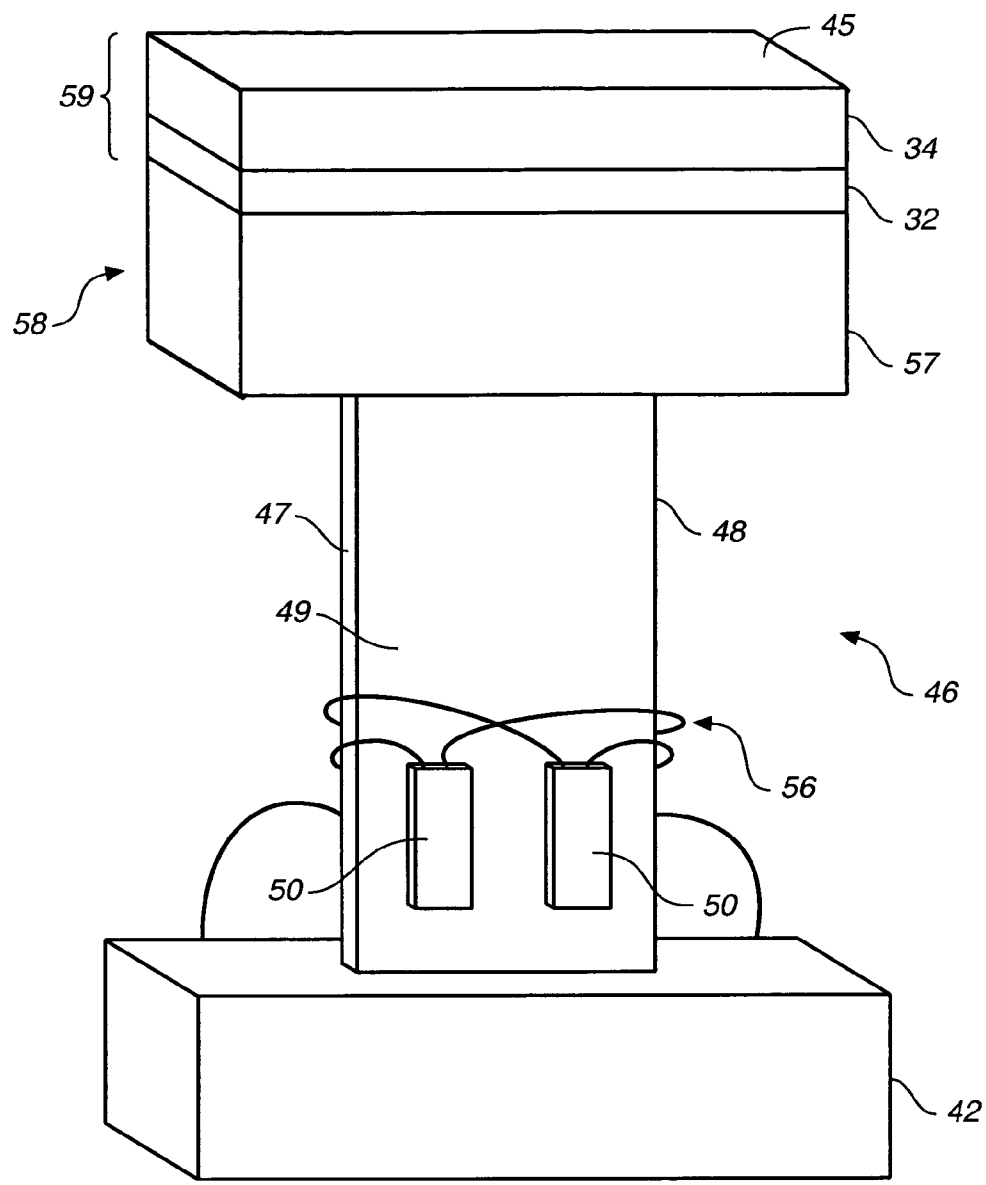
*FIG._4A*
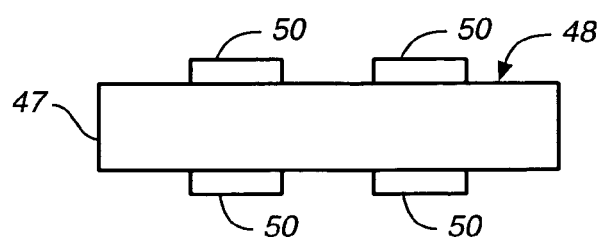
*FIG._4B*

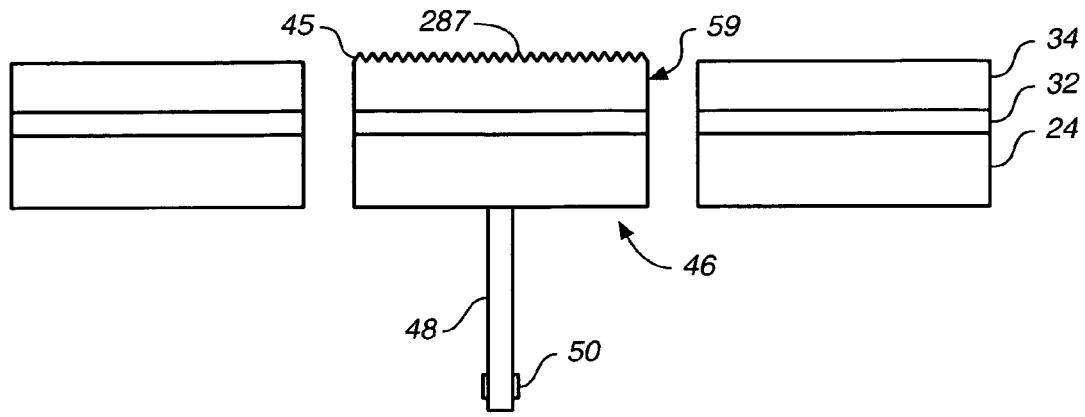
FIG._4C
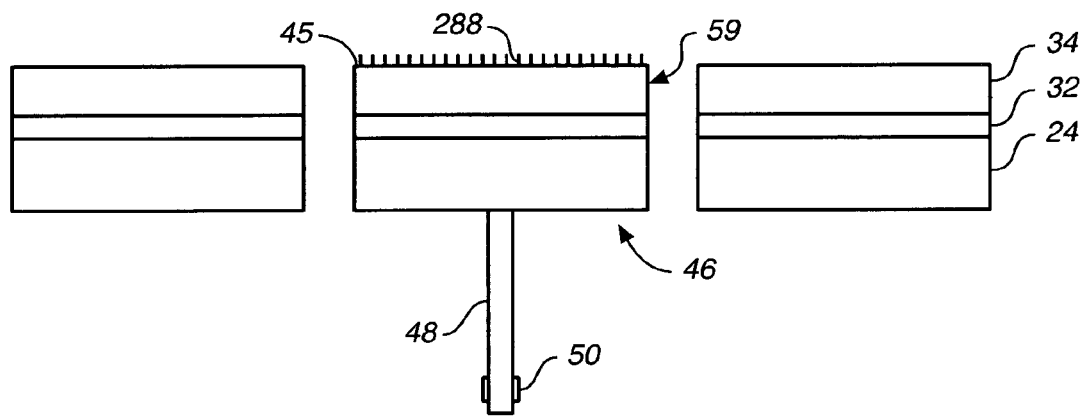
FIG._4D
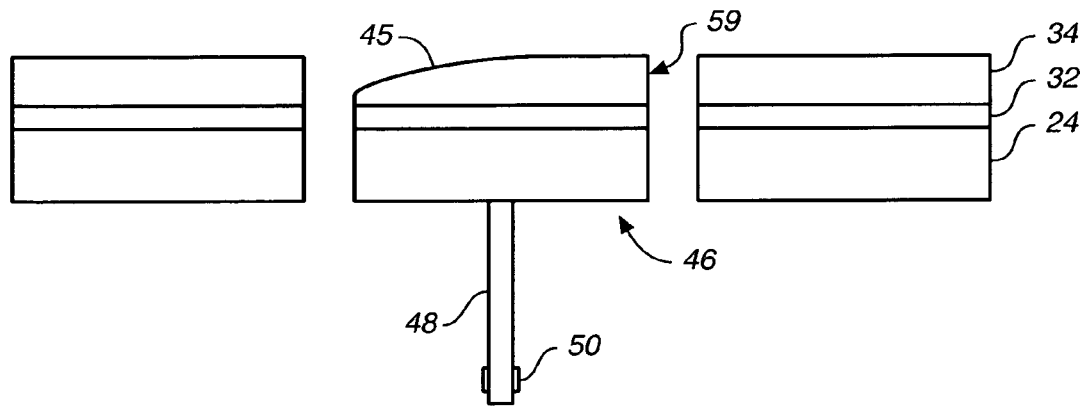
FIG._4E

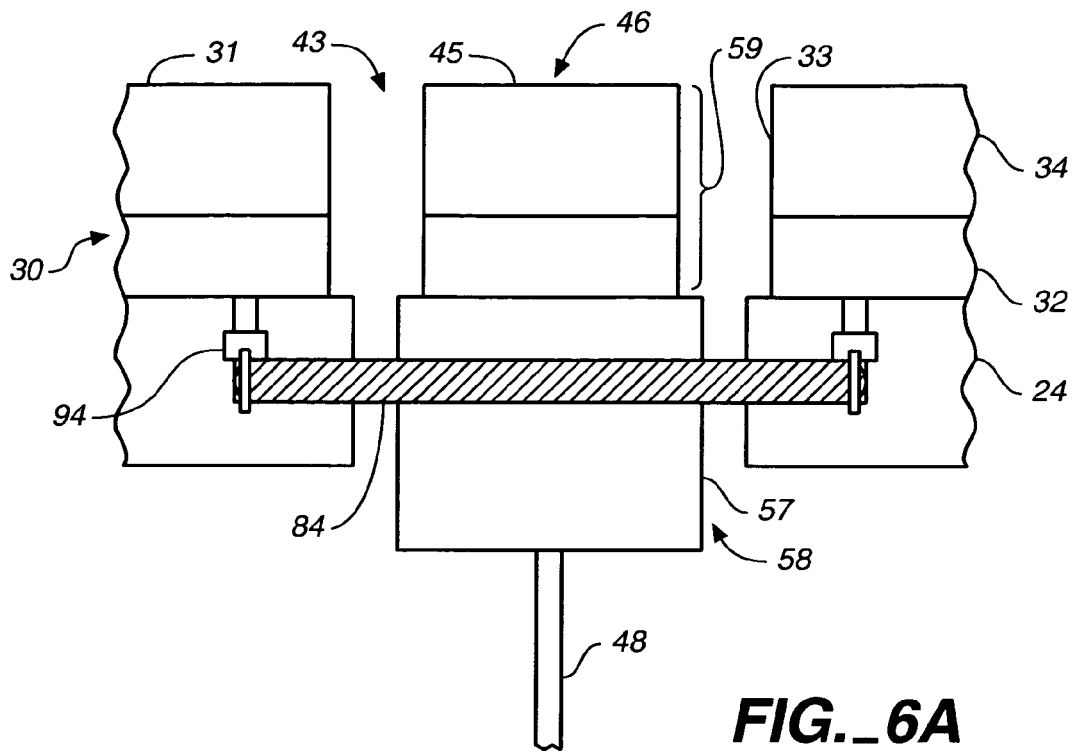
FIG._6A
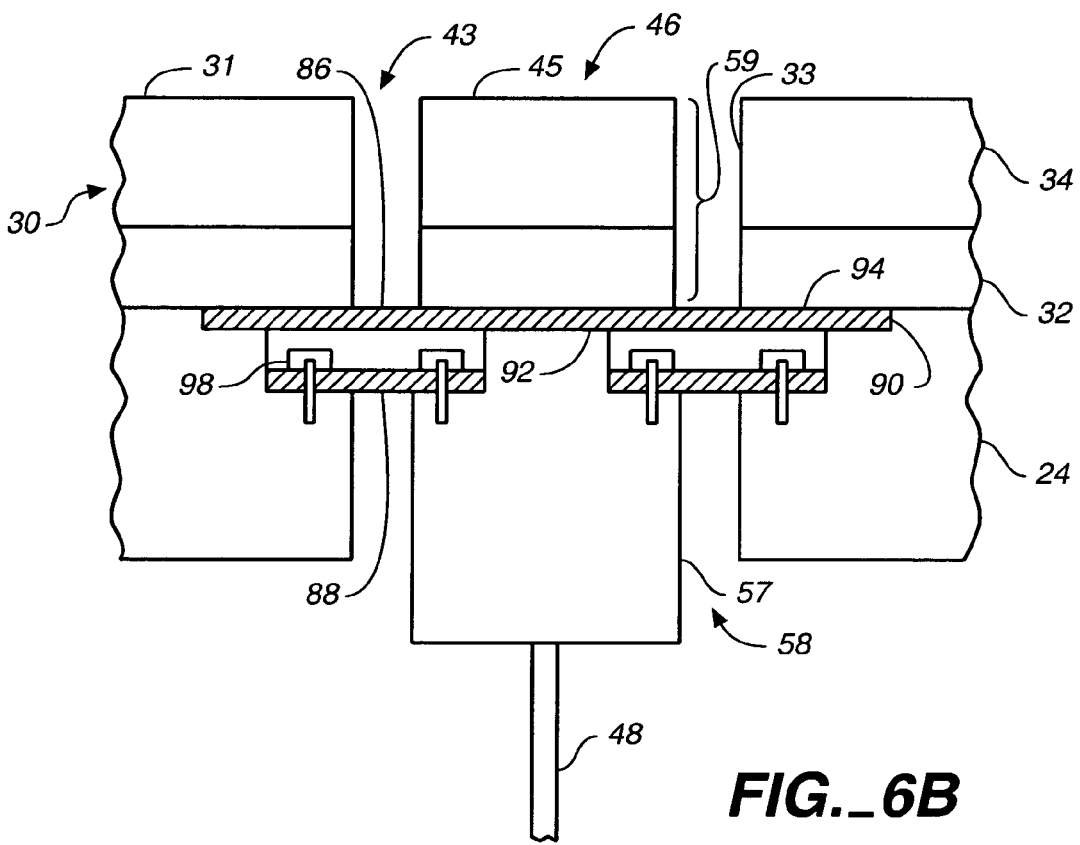
FIG._6B

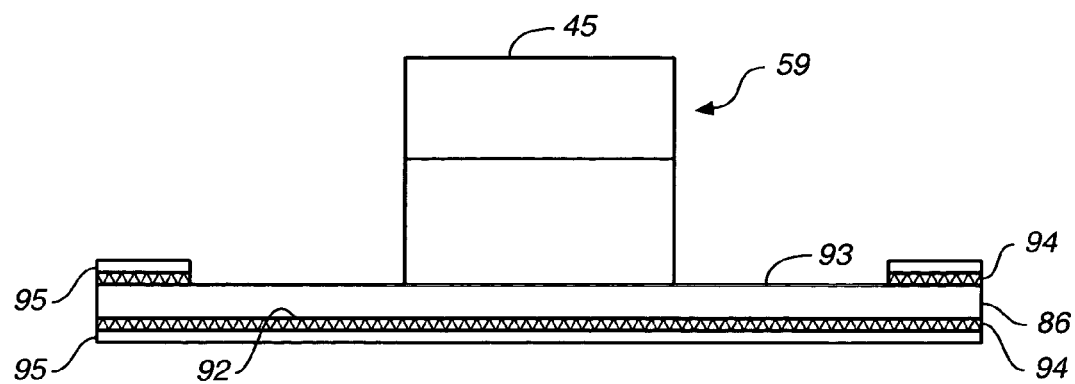
FIG._6C
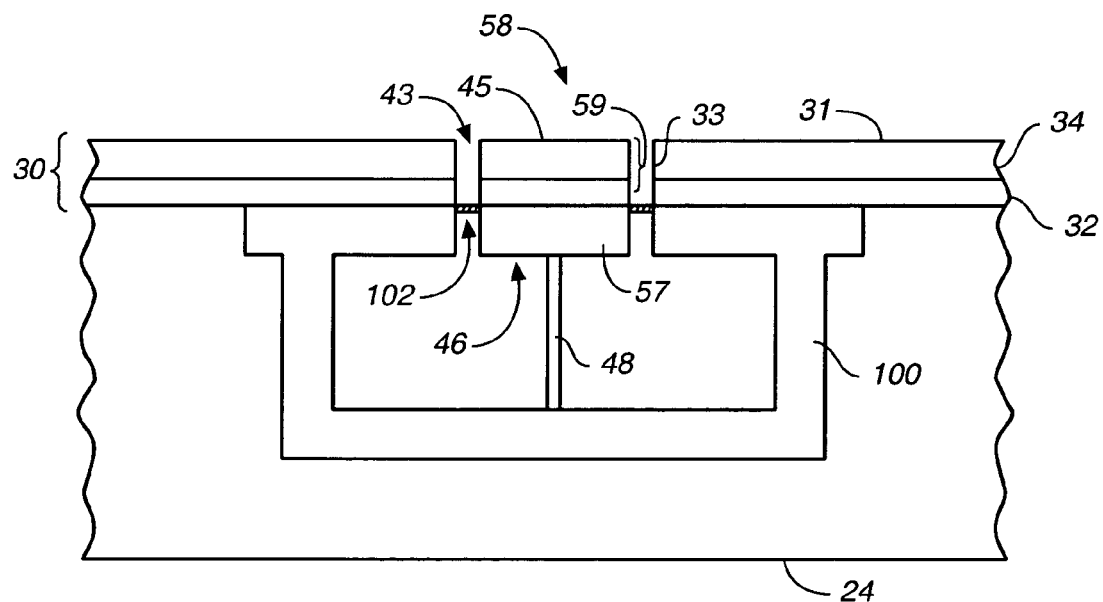
FIG._6D

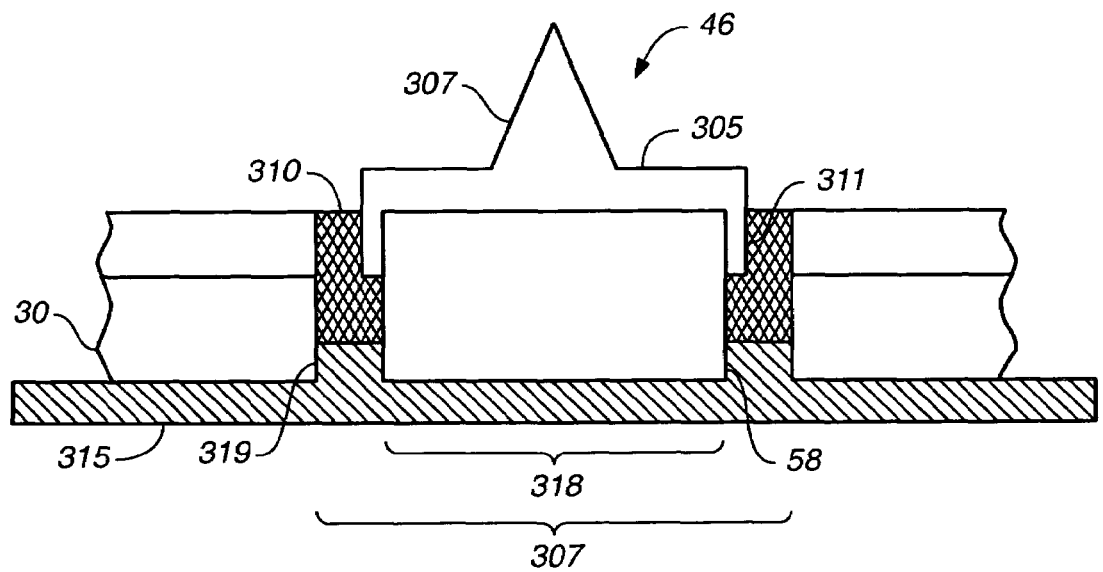
FIG._6E
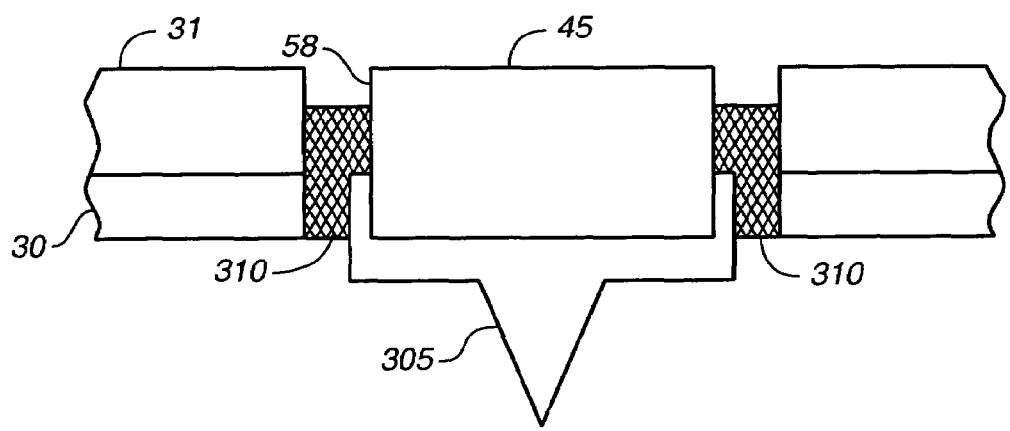
FIG._6F

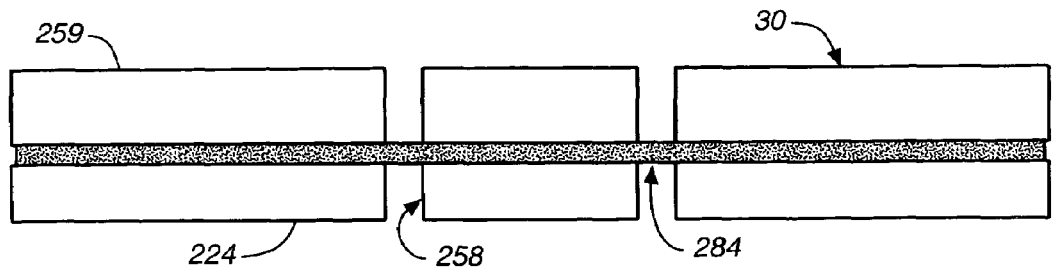
FIG._6G
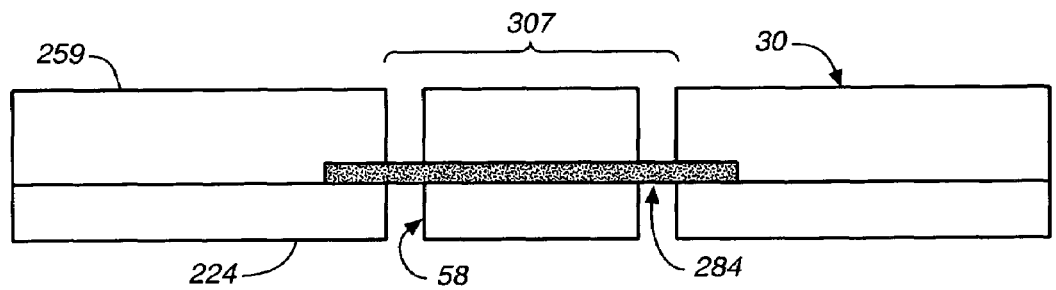
FIG._6H
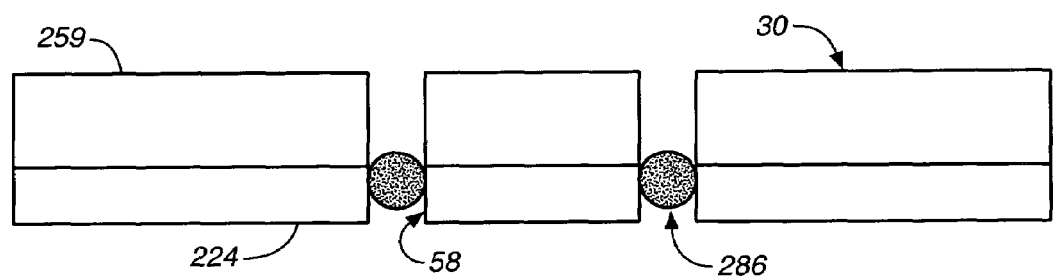
FIG._6I
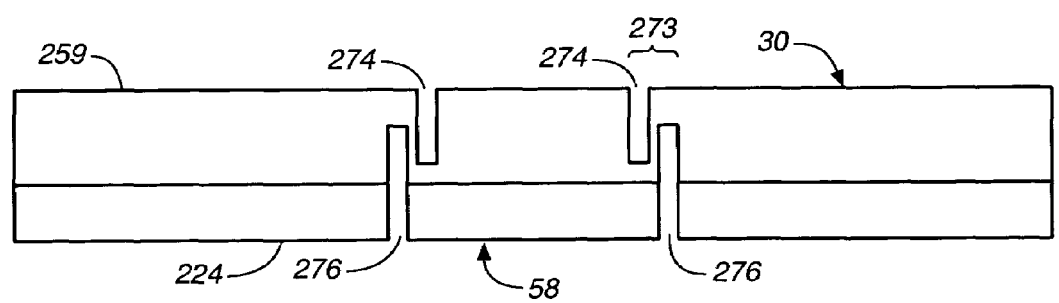
FIG._6J

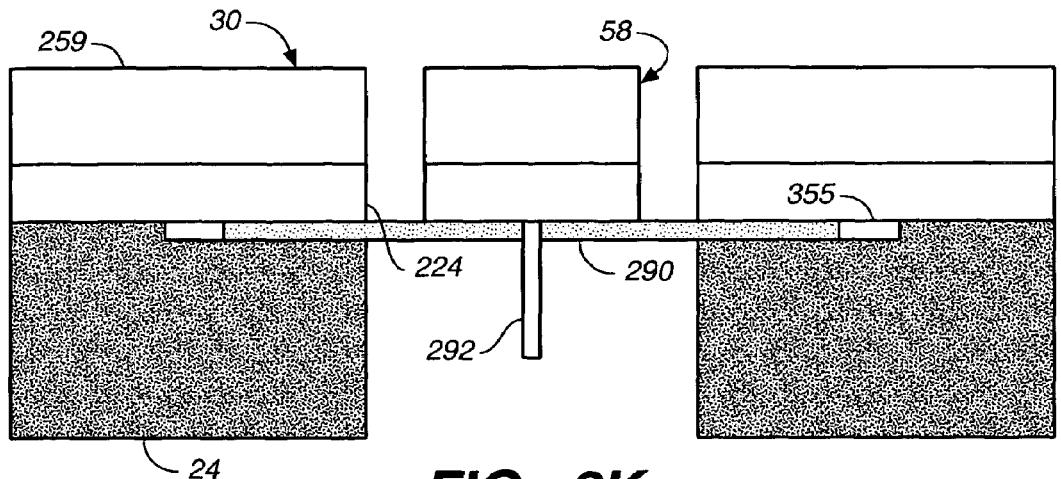
FIG._6K
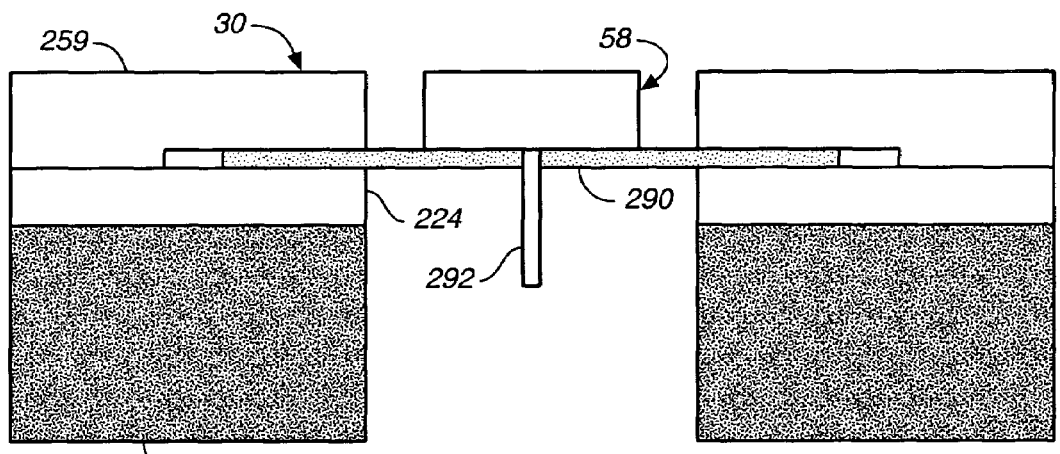
FIG._6L
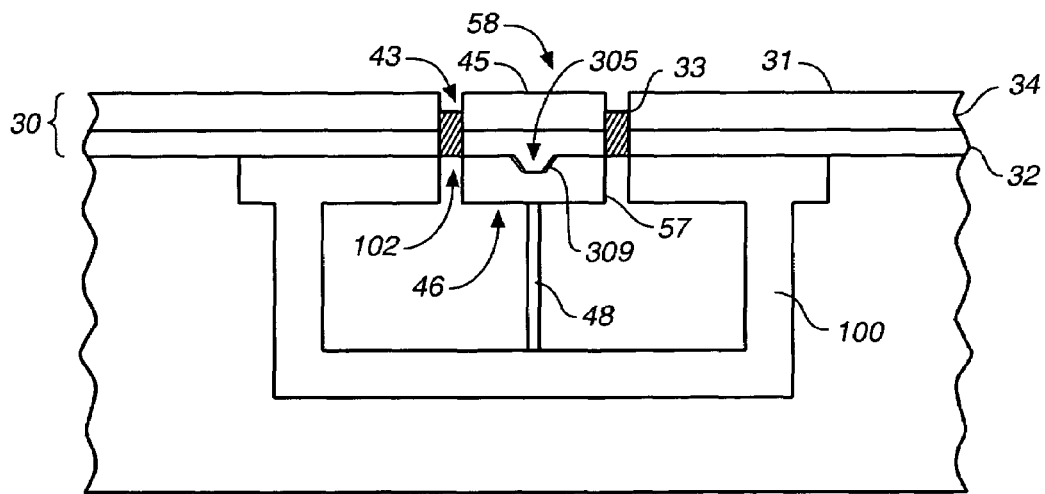
FIG._6M

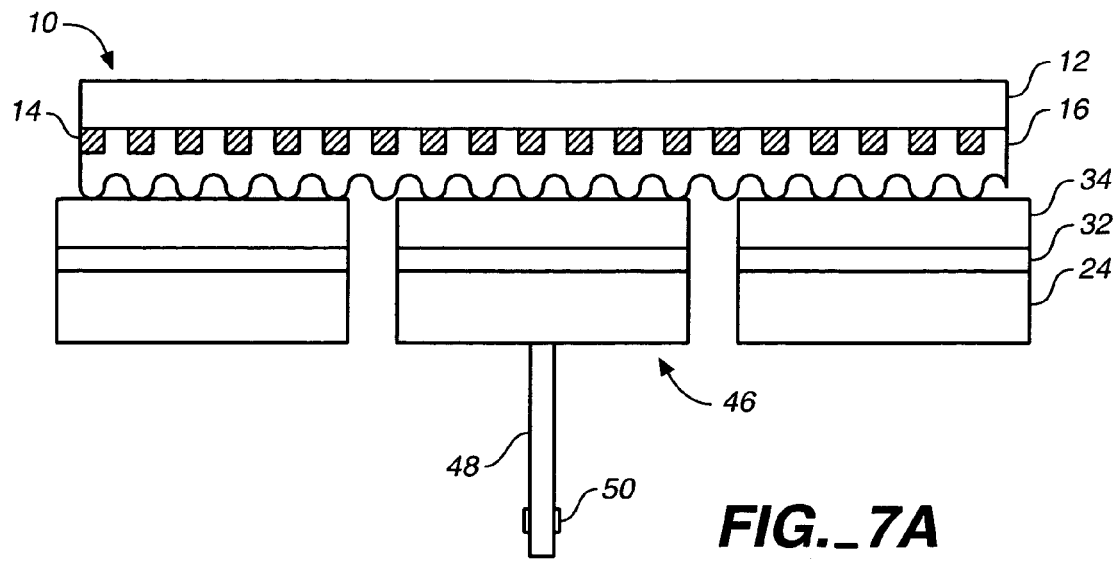
FIG._7A
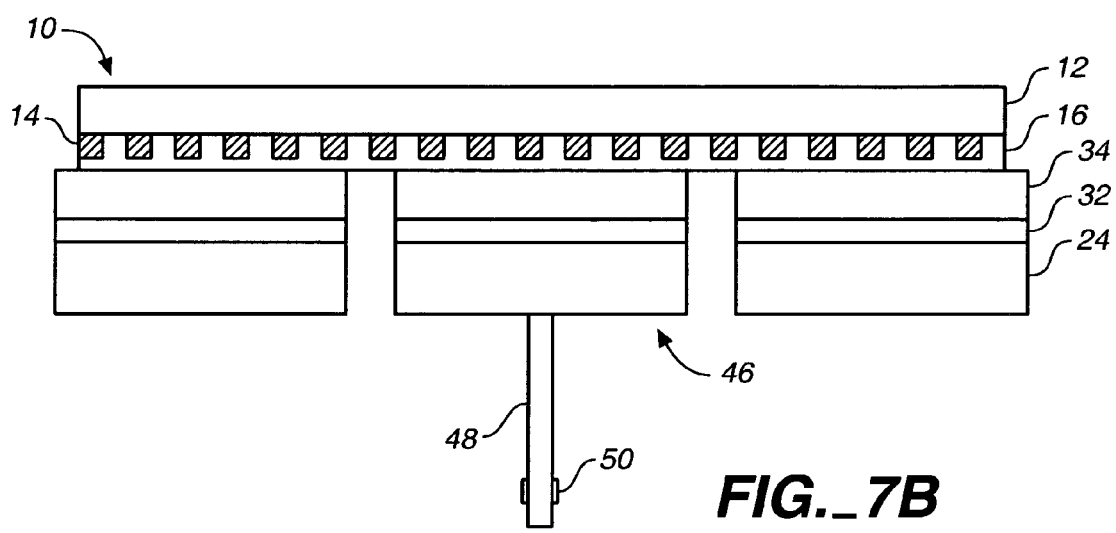
FIG._7B
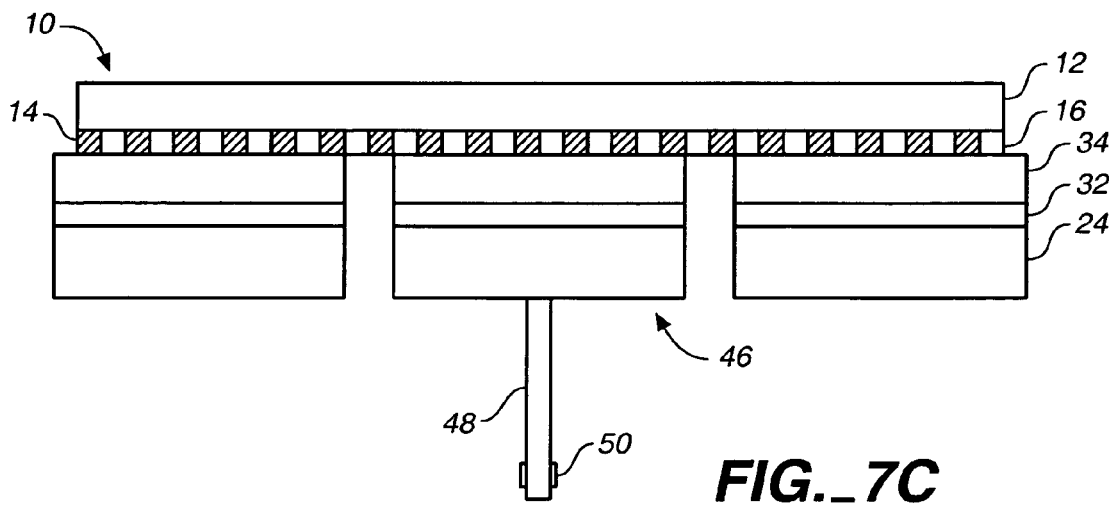
FIG._7C

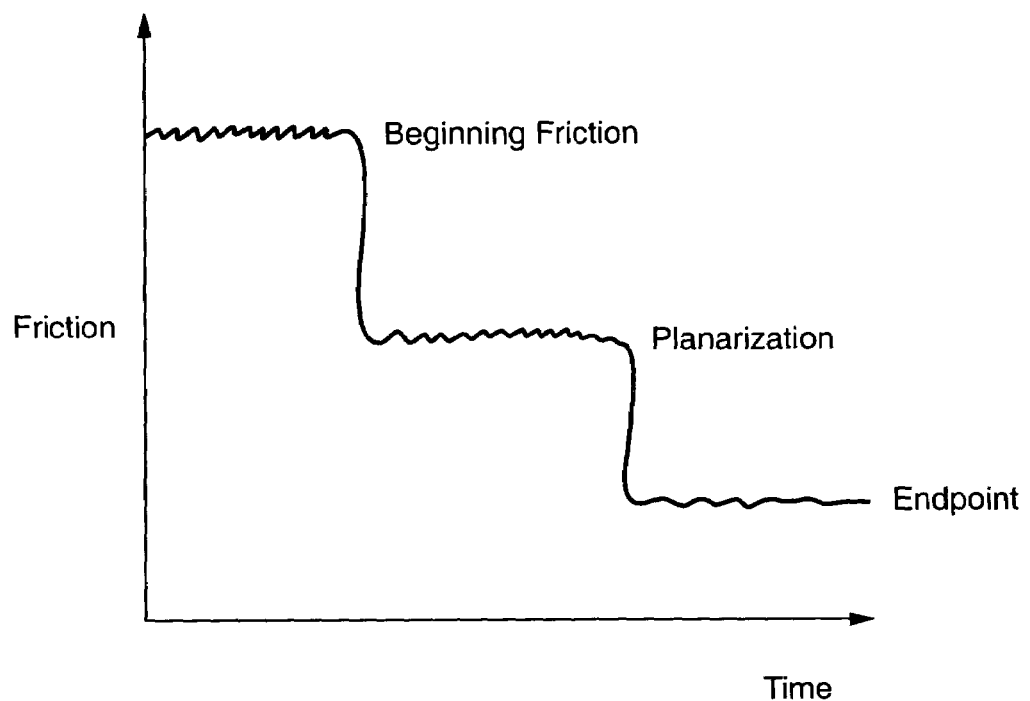
FIG._8A
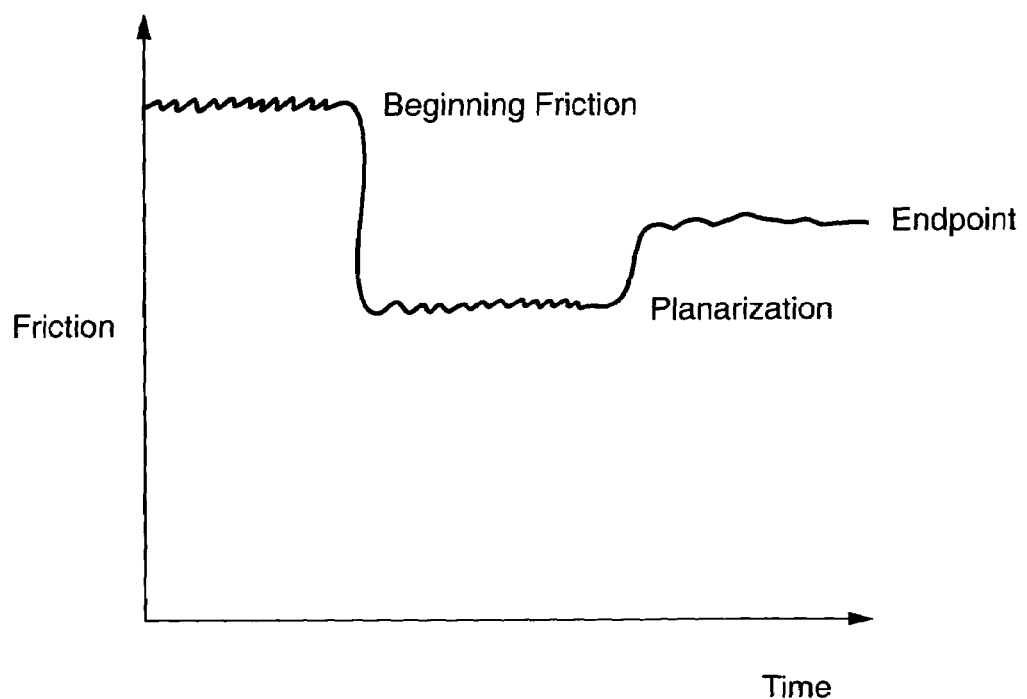
FIG._8B

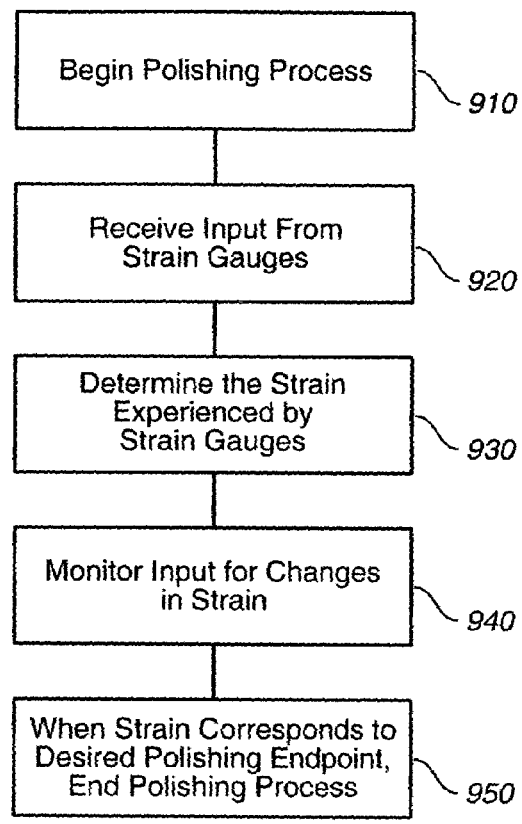
FIG._9
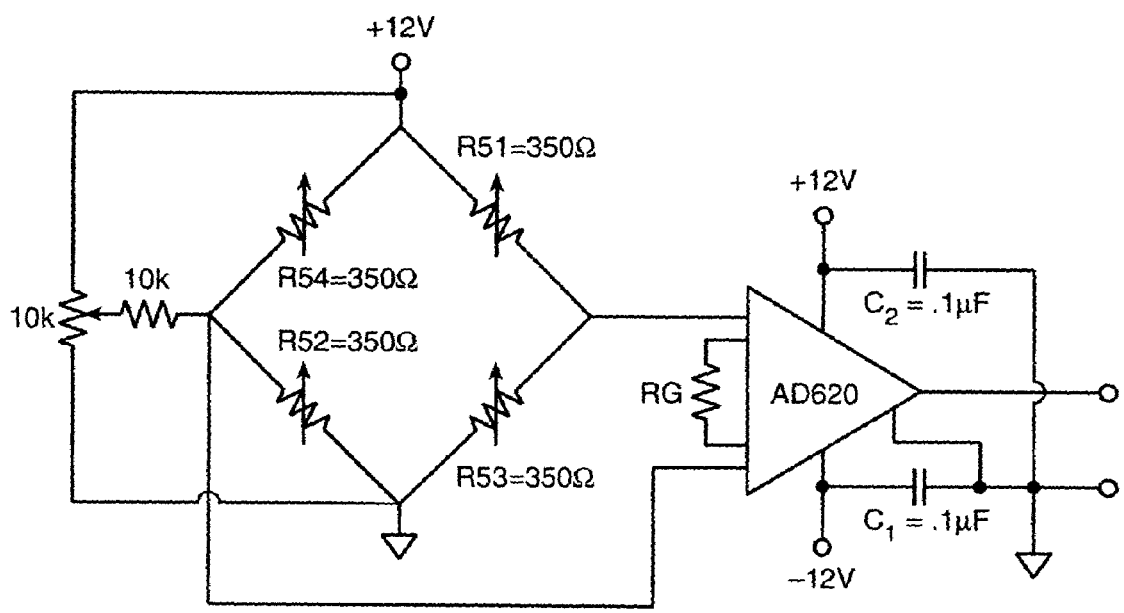
FIG._10

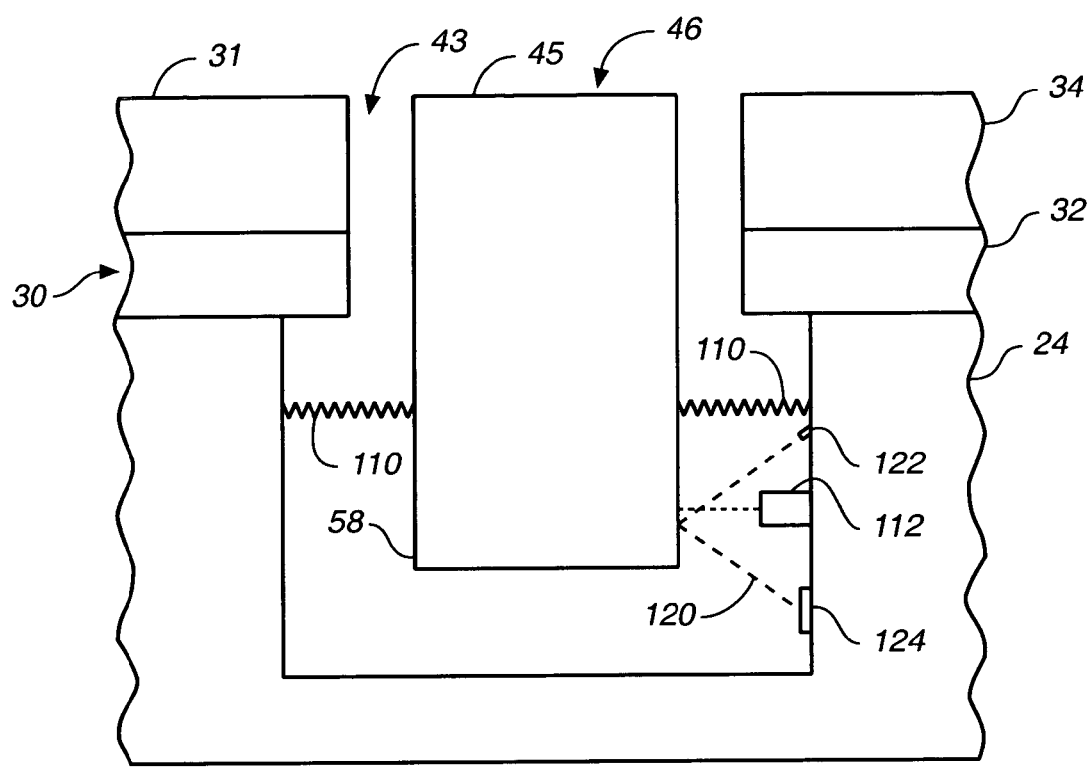
FIG._11
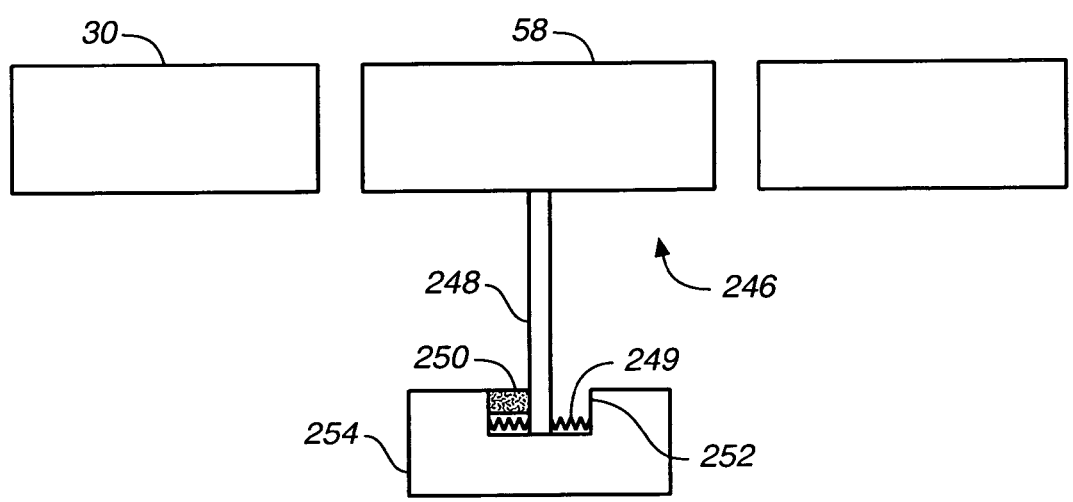
FIG._12

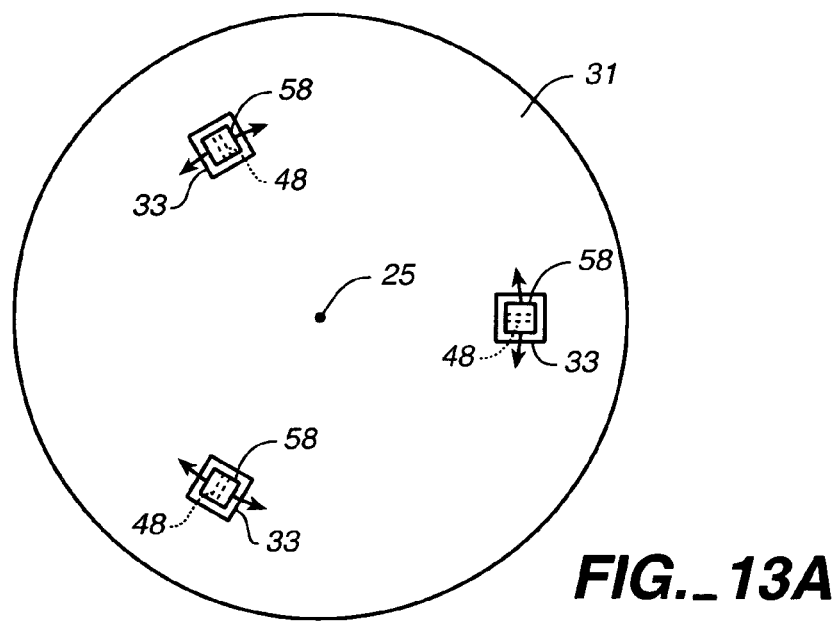
FIG._13A
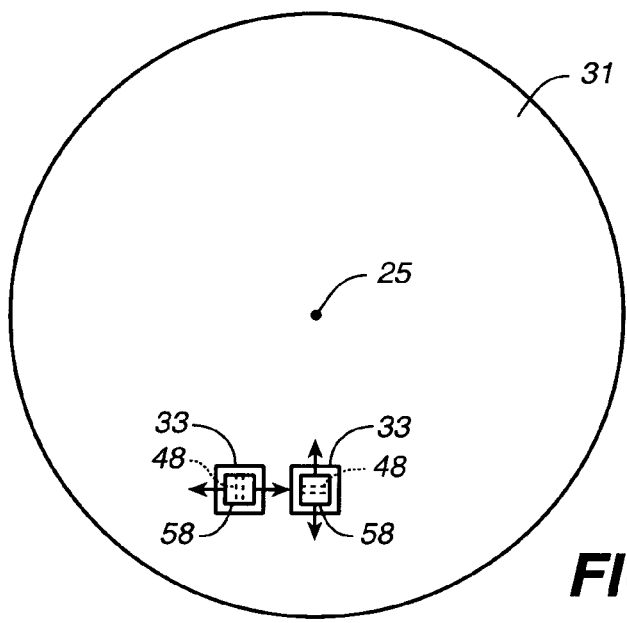
FIG._13B
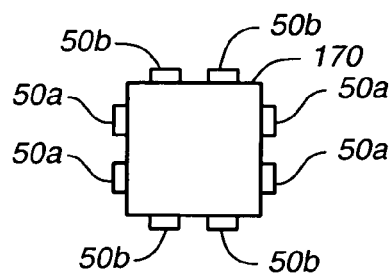
FIG._14

POLISHING ENDPOINT DETECTION SYSTEM AND METHOD USING FRICTION SENSOR

CROSS-REFERENCE TO RELATED APPLICATIONS

This application claims priority to U.S. Provisional Application Ser. No. 60/516,349, filed on Oct. 31, 2003, and to U.S. Provisional Application Ser. No. 60/590,471, filed on Jul. 22, 2004.

BACKGROUND

This invention relates to chemical mechanical polishing of substrates.

An integrated circuit is typically formed on a substrate by the sequential deposition of conductive, semiconductive or insulative layers on a silicon wafer. One fabrication step involves depositing a filler layer over a non-planar surface, and planarizing the filler layer until the non-planar surface is exposed. For example, in a Shallow Trench Isolation (STI) process an oxide filler layer can be deposited on a patterned nitride layer to fill the trenches or holes in the nitride layer (and underlying silicon). The filler layer is then polished until the raised pattern of the nitride layer is exposed. After planarization, the portions of the oxide layer remaining provide isolation between circuits on the substrate. In addition, planarization is needed to planarize the substrate surface for photolithography.

Chemical mechanical polishing (CMP) is one accepted method of planarization. This planarization method typically requires that the substrate be mounted on a carrier or polishing head. The exposed surface of the substrate is placed against a polishing surface such as a rotating polishing disk pad or belt pad. The polishing surface can be either a "standard" pad or a fixed-abrasive pad. A standard pad has a durable roughened surface, whereas a fixed-abrasive pad has abrasive particles held in a containment medium. The carrier head provides a controllable load on the substrate to push it against the polishing pad. A polishing slurry, including at least one chemically-reactive agent, and abrasive particles if a standard pad is used, is supplied to the polishing surface.

One problem in CMP is determining whether the polishing process is complete, i.e., whether a substrate layer has been planarized to a desired flatness or thickness, when a desired amount of material has been removed, or when an underlying layer has been exposed. Variations in the initial thickness of the substrate layer, the slurry composition, the polishing pad condition, the relative speed between the polishing pad and the substrate, and the load on the substrate can cause variations in the material removal rate. These variations cause variations in the time needed to reach the polishing endpoint. Therefore, the polishing endpoint cannot be determined merely as a function of polishing time.

One way to determine the polishing endpoint is to remove the substrate from the polishing surface and examine it. For example, the substrate can be transferred to a metrology station where the thickness of a substrate layer is measured, e.g., with a profilometer or a resistivity measurement. If the desired specifications are not met, the substrate is reloaded into the CMP apparatus for further processing. This is a time-consuming procedure that reduces the throughput of the CMP apparatus. Alternatively, the examination might reveal that an excessive amount of material has been removed, rendering the substrate unusable.

More recently, in-situ monitoring of the substrate has been performed, e.g., with optical or capacitance sensors, in order to detect the polishing endpoint. Other proposed endpoint detection techniques have involved measurements of friction, motor current, slurry chemistry, acoustics, conductivity, and induced eddy currents. However, techniques relying on detection of a change in conductivity or reflectivity between two substrate layers deposited upon a substrate are ineffective when the two layers have similar conductivity and reflectivity.

SUMMARY

In general, in one aspect, the invention is directed to an apparatus to monitor a frictional coefficient of a substrate undergoing polishing. The apparatus includes a movable member having a top surface to contact an exposed surface of a substrate, and a sensor to generate a signal based on a lateral displacement of the movable member. The member is laterally displaceable in response to a frictional force from the substrate and includes a top surface having a surface area less than a surface area of the exposed surface of the substrate.

Implementations of the apparatus may include one or more of the following features. A restorative material, such as leaf spring or plurality of springs, may be coupled to the movable member. The movable member may include a polishing pad segment. The polishing pad segment may include two layers. The movable member may include a support piece coupled between the restorative material and the polishing pad segment. The sensor used to generate a signal based on a lateral displacement of the movable member may be a strain gauge. A plurality of strain gauges may be attached to the leaf spring at the point of maximum strain. The sensor used to generate a signal based on a lateral displacement of the movable member may be an optical sensor, such as a laser interferometer, or a piezoelectric sensor. The top surface of the movable member may be substantially coplanar with a polishing surface of a polishing pad. The movable member may be connected to a platen, e.g., a rotatable platen. The movable member may be separated by a gap from the platen. A flexible sealing membrane may be coupled to the movable member for preventing the transmission of a slurry through the gap. The flexible sealing membrane may be interposed between the restorative material and the movable member.

In general, in another aspect, the invention is directed to an apparatus to monitor a frictional coefficient of a substrate undergoing polishing. The apparatus includes a member having a top surface to contact an exposed surface of the substrate, a restorative material connecting the member to a structure, and a sensor to generate a signal based on a strain of the restorative material. The top surface has a surface area less than a surface area of the exposed surface of the substrate.

In general, in another aspect, the invention is directed to a chemical mechanical polishing apparatus. The apparatus includes a support for a polishing article, a carrier to hold a substrate against a polishing surface of the polishing article, a motor coupled to at least one of the polishing article and carrier for generating relative motion there between, and a sensor for measuring strain. The sensor includes a movable member having a top surface to contact an exposed surface of the substrate, the member laterally displaceable in response to a frictional force from the substrate, the top surface having a surface area less than a surface area of the exposed surface the substrate, and a sensor to generate a signal based on a lateral displacement of the movable member.

Implementations of the invention may include one or more of the following features. The top surface may be substantially coplanar with the polishing surface when the polishing article is held by the support.

In general, in another aspect, a platen for use in a chemical mechanical polishing apparatus is provided. The platen includes a base plate having a recess for housing a strain sensor, the recess having a cross sectional area greater than the cross sectional area of the strain sensor to allow for displacement of the strain sensor. Also included is the strain sensor placed within the recess, the strain sensor including a restorative material having a cross sectional area less than that of the polishing surface that sometimes contacts the substrate either directly or through another material having a cross sectional area less than that of the polishing surface coupled to the restorative material and at least one device for measuring the strain of the restorative material in the direction of relative motion between the substrate and the sensor for measuring strain.

In another aspect, the invention is directed to an article for use in a polishing system. The article has a flexible, fluid-impermeable membrane and a polishing pad piece secured to a first surface of the membrane. The edges of the membrane extending beyond the edges of the polishing pad piece.

Implementations of the invention may include one or more of the following features. An adhesive may be located on second surface of the membrane opposite the first surface and/or on the first surface of the membrane surrounding the polishing pad piece. A removable liner may cover the adhesive. The polishing pad piece may include a cover layer and a backing layer, and the backing layer may be more compressible than the cover layer. The membrane may be silicone or latex.

In one aspect, the invention features a system to monitor a frictional coefficient of a substrate undergoing polishing. A polishing pad assembly includes a polishing layer including a polishing surface, and a substrate contacting member flexibly coupled to the polishing layer having a top surface to contact an exposed surface of a substrate. At least a portion of the top surface is substantially coplanar with the polishing surface. A sensor is provided to measure a lateral displacement of the substrate contacting member.

Implementations may include one or more of the following features. The polishing pad assembly may have an aperture therethrough. The substrate contacting member may be positioned within the aperture. The sensor may include a strain gauge or a pressure gauge. An alignment device may be coupled between the substrate contacting member and the sensor. The polishing pad may surround, but not contact, the substrate contacting member. A seal may extend between the substrate contacting member and the polishing pad. The seal includes a flexible, fluid-impermeable material. The seal may be made of silicone, latex, or polyurethane. The seal may be an O-ring, and the O-ring may be secured to the substrate contacting member and the polishing pad with an adhesive material. The seal may extend through the substrate contacting member. The substrate contacting member and polishing layer may be connected by a flexure that mechanically decouples the substrate contacting member from the polishing pad. The flexure may be formed by recesses in opposite surfaces of the polishing pad.

In another aspect, the invention features a polishing system. The system includes a movable platen. A polishing pad is connected to the movable platen, and the polishing pad has a polishing surface and an aperture therein. A substrate contacting member is contained within the aperture and has a top surface to contact an exposed surface of a substrate. The top surface of the substrate contacting member is substantially coplanar with the polishing surface. A sensor measures a lateral displacement of the substrate contacting member and generate a signal based on the lateral displacement of the substrate. A controller receives the signal from the sensor.

Implementations may include one or more of the following features. The sensor may be a strain gauge or a pressure gauge. An alignment device may be coupled between the substrate contacting member and the sensor. The polishing pad has a top surface to contact the exposed surface of the substrate. The polishing pad may surround, but not contact, the substrate contacting member. A sealing piece may extend between the substrate contacting member and the polishing pad. The sealing piece may be made of a flexible, fluid-impermeable material. The sealing piece may be made of silicone, latex, or polyurethane. The sealing piece may be an O-ring. The O-ring may be secured to the substrate contacting member and the polishing pad with an adhesive material. The sealing piece may extend through the substrate contacting member. The polishing pad may have a top surface to contact the exposed surface of the substrate, and the polishing pad may be made from the same piece of material as the substrate contacting member. A flexure may mechanically isolate the substrate contacting member from the polishing pad.

In another aspect, the invention features an article for use in a polishing system. A polishing pad has a polishing surface. A substrate contacting member has a top surface to contact an exposed section of substrate. The top surface is substantially coplanar with the polishing surface. A seal formed of a flexible and fluid-impermeable material secures the substrate contacting member to the polishing pad and permits the substrate contacting member to move laterally relative to the polishing pad.

Implementations may include one or more of the following features. The polishing pad may have two or more layers. The seal may be secured between two layers of the polishing pad piece. The seal may extend through the entire polishing pad piece, or may extend only partially into the polishing pad piece. A first surface of an alignment device may be attached to the substrate contacting member. The sealing material may also be in contact with the alignment device. An alignment rod may extend from a second surface of the alignment device. The top surface of the substrate contacting member may be composed of the same material as the polishing pad. The top surface of the substrate contacting member may includes grooves that channel liquid away from the substrate contacting member. The seal may an O-ring. The seal may be comprised of latex, silicone, or polyurethane. The polishing pad and the substrate contacting member may be manufactured from one continuous piece of material.

In another aspect, the invention features an apparatus to monitor a frictional coefficient of a substrate undergoing polishing. A movable member has a top surface to contact an exposed surface of a substrate. The top surface had a surface area less than a surface area of the exposed surface of the substrate. A connecting member is coupled to the movable member. The connecting member is laterally displaceable along a channel in response to a frictional force from the substrate. A sensor generates a signal based on a lateral displacement of the connecting member along the channel.

Implementations may include one or more of the following. The movable member may include a polishing pad segment. The sensor may generate a signal based on a lateral displacement of the connecting member is a strain gauge. The top surface of the movable member may be substantially coplanar with a polishing surface of a polishing pad. An anchoring device may be coupled between the polishing pad segment and the connecting member. The anchoring device may be coupled to the connecting member by means of an alignment rod. A flexible, fluid-impermeable membrane may be located between the anchoring device and the connecting member, so that polishing slurry does not enter the channel or the sensor. The membrane may be silicone, latex, or polyurethane.

In another aspect, the invention features a method of assembling a polishing pad. A substrate contacting member is aligned in a mold. The mold has a raised rim, such that the substrate contacting member is aligned with an inside surface of the raised rim. A polishing pad having an opening is aligned with an outside surface of the raised rim, such that the opening is aligned with the outside surface of the raised rim. A sealing material is placed inside a recess formed by the substrate contacting member, the polishing pad, and the raised rim.

Implementations may include one or more of the following features. An alignment device may be aligned with the substrate contacting member, such that a first surface of the alignment device is attached to the substrate contacting member and the sealing material is also in contact with the alignment device. An alignment rod may extend from a second surface of the alignment device. A top surface of the substrate contacting member may be composed of the same material as the polishing pad. The top surface of the substrate contacting member may include grooves that channel liquids away from the substrate contacting member. The sealing material may be an O-ring. The sealing material may be latex, silicone, or polyurethane.

In still another aspect, the invention is directed to an apparatus to monitor a frictional coefficient of a substrate during a polishing operation. The apparatus has a member to engage a region of a surface of a substrate undergoing polishing. The region has a surface area less than a surface area of the surface of the substrate, and the member is laterally movable relative to a polishing surface.

Implementations may include one or more of the following features. The apparatus may include a means for generating a signal indicating a lateral frictional force of the substrate on the member. The may comprise a portion of a polishing pad or a body that is movably connected to a platen. The member may be laterally movable in substantially a single direction, or laterally movable in two perpendicular directions.

In still another aspect, the invention is directed to a method of monitoring a frictional coefficient of a substrate during a polishing operation. The method includes positioning a surface of a substrate in contact with a polishing surface and simultaneously in contact with a top surface of a member that is laterally movable relative to the polishing surface, and generating a signal indicating a lateral frictional force of the substrate on the member.

These general and specific aspects may be implemented using a system, a method, or an apparatus, or any combination of systems, methods, and apparatus. Moreover, any of the various features described above may be used in combination with other features or with other aspects of the invention.

The present invention can be implemented to realize some, all, or none of the following advantages. A chemical mechanical polishing system or apparatus incorporating the present invention can provide accurate endpoint detection during chemical mechanical polishing to indicate the planarization of a layer or the exposure of an underlying layer. Additionally, the present invention can provide endpoint detection during a polishing process in which the layer being polished is not conductive. Further, the present invention can provide endpoint detection during a polishing process in which the layer being polished and the layer to be exposed have similar optical properties, such as reflectivity and refractive index. Specifically, the present invention can provide endpoint detection during a Shallow Trench Isolation (STI) polishing process in which a silicon dioxide layer is being polished to expose a silicon nitride layer. The present invention can also provide endpoint detection in a polishing process on which the layer being polished and the layer to be exposed have similar conductive properties.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic exploded perspective view of a chemical mechanical polishing apparatus.

FIG. 2 is a schematic side view, partially cross-sectional, of a chemical mechanical polishing apparatus including a friction sensing system.

FIG. 3 is a schematic top view of a chemical mechanical polishing apparatus including a strain sensor.

FIG. 4A-4B are schematic side views, partially cross-sectional, of a strain sensor.

FIG. 4C-4E are schematic side views of a polishing pad with a strain sensor.

FIG. 5 is a schematic circuit diagram of a strain measuring device.

FIGS. 6A, 6B, 6D and 6M are schematic cross-sectional views of a strain sensor.

FIG. 6C is a schematic cross-sectional view of an article to install in the polishing apparatus.

FIG. 6E schematically illustrates a method of assembling a polishing pad with patch pad sensor.

FIG. 6F-6J are schematic cross-sectional views of articles to install in the polishing apparatus.

FIG. 6K-6L are schematic cross-sectional views of a two-piece polishing pad with shroud sealing layer.

FIG. 7A-7C schematically illustrate a method of detecting a polishing endpoint using a strain sensor.

FIG. 8A-8B are graphs illustrating an example trace of friction versus time for a polishing process.

FIG. 9 illustrates a flowchart for carrying out a method of chemical mechanical polishing using a strain sensor.

FIG. 10 is a schematic circuit diagram of an implementation of a strain gauge bridge and amplifier circuit.

FIG. 11 is a schematic side view, partially cross-sectional, of an alternative implementation of a strain sensor.

FIG. 12 is a schematic side view, partially cross-sectional, of another alternative implementation of a friction sensor.

FIG. 13A is a schematic top view of a polishing station with multiple sensors.

FIG. 13B is a schematic top view of a polishing station with multiple sensors to measure friction in orthogonal directions.

FIG. 14 is a schematic top view of a strain sensor with a support post.

Like reference symbols in the various drawings indicate like elements.

DETAILED DESCRIPTION

Referring to FIGS. 1 and 2, one or more substrates 10 can be polished by a CMP apparatus 20. A description of a similar polishing apparatus 20 can be found in U.S. Pat. No. 5,738, 574, the entire disclosure of which is incorporated herein by reference. Polishing apparatus 20 includes a machine base 21 that supports a series of polishing stations 22 and a transfer station 23. Transfer station 23 transfers the substrates between the carrier heads and a loading apparatus.

Each polishing station includes a rotatable platen 24 on which is placed a polishing article, such as a polishing pad 30. The polishing pad 30 can be a two-layer polishing pad with a hard durable outer surface, a single layer hard pad, a fixed-abrasive pad with embedded abrasive particles, or a relatively soft pad. Each polishing station can also include a pad conditioner apparatus 28 to maintain the condition of the polishing pad 30 so that it will effectively polish substrates 10.

A two-layer polishing pad 30, typically has a backing layer 32 which abuts the surface of platen 24 and a covering layer 34 with a polishing surface 31 which is used to polish substrate 10. The covering layer 34 is typically harder than the backing layer 32. The covering layer 34 can be composed of foamed or cast polyurethane, possibly with fillers, e.g., hollow microspheres, and/or a grooved surface. The backing layer 32 can be composed of compressed felt fibers leached with urethane. A two-layer polishing pad, with the covering layer composed of IC-1000 and the backing layer composed of SUBA-4, is available from Rodel, Inc., of Newark, Del. (IC-1000 and SUBA-4 are product names of Rodel, Inc.).

A rotatable multi-head carousel 60 supports four carrier heads 70. The carousel is rotated by a central post 62 about a carousel axis 64 by a carousel motor assembly (not shown) to orbit the carrier head systems and the substrates attached thereto between the polishing stations 22 and the transfer station 23. Three of the carrier head systems receive and hold substrates, and polish them by pressing them against the polishing pad 30. Meanwhile, one of the carrier head systems receives a substrate 10 from, and delivers the substrate 10 to, transfer station 23.

Each carrier head 70 is connected by a carrier drive shaft 74 to a carrier head rotation motor 76 (shown by the removal of one quarter of cover 68) so that each carrier head can independently rotate about it own axis. In addition, each carrier head 70 independently laterally oscillates in a radial slot 72 formed in carousel support plate 66. A description of a suitable carrier head 70 can be found in U.S. patent application Ser. No. 10/810,784, filed Mar. 26, 2004, the entire disclosure of which is incorporated by reference. In operation, the platen 24 is rotated about its central axis 25, and the carrier head is rotated about its central axis 71 and translated laterally across the surface of the polishing pad.

A slurry 38 can be supplied to the polishing pad 30 by a slurry supply port or combined slurry/rinse arm 39. If the polishing pad 30 is a standard pad, the slurry 38 can include abrasive particles (e.g., silicon dioxide for oxide polishing).

Now referring to FIGS. 2 and 3, a recess 26 is formed in the platen 24, and an aperture 33 is formed in the polishing pad 30. The recess 26 and aperture 33 are positioned to pass beneath the substrate 10 at some time during a period of relative motion between the polishing pad 30 and the substrate 10. For example, assuming the platen 24 rotates, the recess 26 will follow a path 96 across the substrate 10, thus scanning across the substrate 10.

A friction sensing system, which monitors and detects changes in the frictional coefficient of a localized, discrete area of a substrate, is placed, in part, within the recess 26. The friction sensing system includes a strain sensing mechanism (strain sensor) 46 and a processing device, such as a computer 90, for processing data from the strain sensor 46.

The strain sensor 46 includes a substrate contacting member 58 that can move when subjected to frictional force from the substrate, a restorative material to urge the substrate contacting member back toward a neutral position, and a sensor that generates a signal based on the displacement of the substrate contacting member.

The strain sensor 46 is placed within the recess 26 and extends through the aperture 33 in the polishing pad 30 such that a top surface 45 of the substrate contacting member 58, having a cross sectional area less than that of the substrate 10, rests co-planar with the polishing surface 31 of the polishing pad 30. Assuming the platen 24 rotates, the strain sensor 46 and substrate contacting member 58 will follow the path 96 across the substrate 10. Thus, the surface 45 of the substrate contacting member 58 contacts the substrate 10 at least some of the time, e.g., periodically each rotation of the platen 24.

Again assuming the platen 24 rotates, the strain sensor 46 can be configured so that the substrate contacting member 58 is movable in a direction that is tangent to the circular path traversed by the substrate contacting member 58, but is generally not movable in other directions, perpendicular to the circular path traversed by the substrate contacting member 58.

One implementation of a strain sensor is illustrated in FIG. 4. In this implementation, the restorative material is a leaf spring 48 that is mounted on a base 42. The leaf spring 48 can be formed from a metallic material, such as stainless steel. The leaf spring 48 can be a rectangular solid having a narrow side 47. The thickness of the narrow side 47 and the composition of the leaf spring 48 can be chosen based on the expected frictional forces so that the leaf spring 48 bends elastically (without undergoing inelastic deformation) when the strain sensor 46 is subjected to a frictional force caused by contact with the substrate 10. The leaf spring 48 is oriented within the recess 26 such that the surface of the wide side 49 of the leaf spring 48 is perpendicular to the direction of relative motion between the substrate 10 and the strain sensor 46. The base 42 provides a rigid support for securing the leaf spring 48 within the recess 26 and restricts lateral movement. Frictional drag resulting from the relative motion causes the spring leaf 48 to experience strain in the form of bending.

In particular, the leaf spring 48 can be oriented with the wide side 49 substantially parallel to a radius passing through the axis of rotation 25 of the platen. Thus, the leaf spring 48 can bend along a lateral direction that is tangent to the circular path traversed by the substrate contacting member 58, but is relatively unbendable along other lateral directions, e.g., parallel to the radius.

A gap 43 between the substrate contacting member 58 and the platen 24 provides a space for the substrate contacting member 58 to move as leaf spring 48 bends. The size of the gap 43 in the tangential direction is based on the spring constant of the leaf spring 48 and the expected magnitude of the frictional force exerted on the substrate contacting member 58 by the substrate 10. The gap 43 should provide sufficient space or the substrate contacting member 58 to move without contacting the sidewalls of the recess 26 under the expected polishing conditions (e.g., carrier head downforce, platen rotation rate, and slurry composition).

The substrate contacting member 58 can be attached to a surface of the leaf spring 48 such that the substrate contacting member 58 is co-planar with the polishing pad 30. The substrate contacting member 58 can be a single piece or can include other components, such as a support piece 57 and a polishing pad segment 59, so that the resulting top surface 45 of strain sensor 46 is co-planar with the polishing pad.

In general, the top surface 45 of the substrate contacting member 58 is formed of a material that does not adversely impact the polishing process, e.g., it should be chemically compatible with the polishing environment and sufficiently soft as to avoid scratching or damaging the substrate. For example, a segment 59 of a polishing pad, such as a two part polishing pad including the backing layer 32 and the covering layer 34 as discussed above, having a cross sectional area less than the substrate 10, can be mounted to the support piece 57 and placed atop of the leaf spring 48. The polishing pad segment 59 mounted to the substrate contacting member 58 is then co-planar with the polishing pad 30 mounted on the platen 24.

Generally, the top surface 45 of the polishing pad segment 59 is formed of the same material used for the polishing surface 31 of the polishing pad 30. In one implementation, the top surface 45 may be designed to enhance the performance of the strain sensor 46. For example, as shown in FIG. 4C, the top surface 45 may have a groove pattern 287 or a squeegee-type structure designed to direct the slurry away from the polishing pad segment 59. Alternatively, as shown in FIG. 4D, the top surface 45 may have a brush structure with bristles 288 designed to maintain contact with the substrate.

Referring now to FIG. 4E, the top surface 45 may also be shaped at an angle in order to avoid out-of-plane excursions when the leaf spring 48 of the strain sensor 46 is moved away from equilibrium. As the leaf spring leaves the equilibrium position, some portion of the top surface 45 remains in contact with the substrate. This allows the strain sensor to measure the frictional force caused by contact with the substrate, whether or not the leaf spring is moved away from equilibrium, without generating uneven pressure profiles on the front surface of the substrate.

As noted above, the top surface 45 has a cross sectional area less than that of the substrate 10 (and less than the polishing surface 31). For example, the top surface can be less than 5%, or less than 1% of the surface area of the substrate. The top surface 45 can have a surface area of about 0.20 cm$^2$ to 10 cm$^2$, e.g., the top surface 45 can be a square about 0.5 to 3 cm on a side or a circle with a similar diameter.

Relative motion between the substrate 10 and the polishing pad 30 cause the substrate contacting member 58 of the strain sensor 46 to intermittently come into physical contact with the substrate 10. The contact generates a frictional force on the strain sensor 46 depending on the coefficient of friction between the strain sensor 46 and the substrate 10. The substrate contacting member 58 is displaceable laterally (i.e. parallel to the surface of substrate 10 and polishing pad 30) under the effect of a frictional force and this lateral displacement results in a strain upon the leaf spring 48. The amount of strain experienced by the leaf spring 48 depends upon the frictional force exerted on the strain sensor 46 by the substrate 10. The frictional force depends in part upon both the nature of the substrate material and also upon the degree of planarization of the substrate. The percentage deformation from the original shape of the leaf spring 48 reflects the degree of strain. The strain of the leaf spring 48 can be measured by monitoring this deformation. In one implementation, the leaf spring 48 can be designed such that the relationship of deformation to applied frictional force is linear, at least to the range of forces that would be expected in the polishing operation.

A device for measuring the strain or displacement of the leaf spring 48 can be included within the recess 26. For example, strain or displacement measuring devices can measure strain based on optical monitoring of the position of the leaf spring 48, detection of changes in the physical properties of the leaf spring 48, such as conductivity, or through the use of attached strain gauges. In one implementation, the strain sensor 46 includes multiple strain gauges 50 adhered to leaf spring 48. The strain gauges 50 can be interconnected through leads 56 to other strain gauges 50 on the opposite side of the leaf spring 48 and coupled to an output system (not shown).

When frictional forces between the substrate contacting piece 58 and the substrate 10 cause the leaf spring 48 to bend the strain gauges 50 will also bend, experiencing the same strain as the leaf spring 48 at the point of attachment. The strain gauges 50 on one surface of the leaf spring 48 will be extended, whereas the strain gauges 50 on the opposite side of the leaf spring 48 will be compressed. As a result the strain gauges will generate a signal proportional to the strain on the leaf spring 48.

An exemplary strain gauge 50 contains a length of wire and is fastened by an adhesive directly to the object, the strain of which is to be measured, in this case the leaf spring 48. The length of wire can be longer than the strain gauge itself by placing the wire in a serpentine path within the strain gauge 50. The compression or extension of the length of wire in each strain gauge 50 will alter the wire's conductive properties. As the length of wire is extended, the resistance increases. Conversely, when the length of wire is compressed, resistance decreases.

In one implementation of the strain sensor 46, four strain gauges 50 are used. Two strain gauges 50 are placed on one surface of the leaf spring 48 while two other strain gauges 50 are placed on the opposite surface of the leaf spring 48. When the leaf spring 48 bends, two strain gauges 50 exhibit increased resistance while two other strain gauges 50, on the opposite side of the leaf spring 48, exhibit decreased resistance.

Referring now to FIG. 5, a strain gauge bridge circuit 52 can be used to schematically represent the interconnections between the strain gauges 50. The strain gauges 50 can be represented as four resistors within the strain gauge bridge circuit having the same base resistance value R. As shown in a generalized bridge circuit in FIG. 5, the strain gauges 50 experiencing increased resistance are represented by R+dR while the strain gauges 50 experiencing decreased resistance are represented by R−dR where dR is the change in. resistance cause by the deformation of the strain gauge 50. The change in circuit voltage as a result of the changed resistance is generally small and can be amplified in some implementations by an amplifier 54 to provide a stronger resulting output signal. The output is indicative of the strain forces acting upon the leaf spring 48.

Referring back to FIGS. 2 and 5, the amplified output of the strain gauge bridge circuit 52 is sent to computer 90 for processing. Processing can include calculation of a frictional coefficient between the polishing pad segment 59 and the substrate 10, associating measurements from the stain sensor 46 with radial positions on the substrate 10, analyzing the progress of a chemical mechanical polishing process based on the strain measurements, controlling the polishing apparatus based on changes in the measured strain, and translating the strain measurements into graphical information. An output can be displayed by a device such as a monitor 92.

Referring to FIG. 2, as discussed above, the gap 43 formed between the strain sensor 46 and the platen 24 allows a space for the strain sensor 46 to move laterally under the frictional force from the substrate 10. Potentially, slurry could flow through this gap into the recess 26. A drain 44 can extend through the platen 24 to remove slurry that accumulates in the recess 26 during the polishing process. The drain 44 can function alone or in combination with an elastic or flexible fluid-impermeable sealing membrane as discussed below with respect to FIGS. 6A-6M.

Referring now to FIGS. 6A-6M, an elastic or flexible fluid-impermeable seal, e.g., a sealing membrane, such as a silicone or latex membrane, can be used to seal the gap between the strain sensor 46 and the platen 24. The sealing membrane prevents slurry from passing through the gap and into the recess 26. Some exemplary sealing implementations are shown in FIGS. 6A-6M.

As shown in FIG. 6A, a sealing membrane 84 forms part of the support piece 57 of the substrate contacting member 58 and is connected to the platen 24 by one or more fasteners 94. The sealing membrane 84 spans the gap between the support piece 57 and the platen 24. The sealing membrane 84 can form a ring encircling the support piece 57 or the sealing membrane 84 can be a solid piece integrated into, or placed on top of, the support piece 57. The fasteners 94 can be mechanical fasteners such as threaded screws, or the fastening can be provided by an adhesive material. A polishing pad segment 59 can be attached to the support piece 57. The polishing pad segment 59 need not be identical to the polishing pad 30 adhered to the platen 24. However, it would be beneficial to use polishing surfaces, on both the platen 24 and as part of the strain sensor 46, having similar characteristics in order to have uniform polishing of the substrate 10. In one implementation, the polishing pad 30 may be flush with the edge of recess 26. Alternatively, the polishing pad 30 may be recessed from the edge as shown in FIG. 6A.

FIG. 6B illustrates an example of a system using two sealing membranes. The first sealing membrane 88 is a ring connected by fasteners 98 to a recess in both the platen 24 and the support piece 57. A second sealing membrane 86 is a solid piece adhered on top of the platen 24 and spanning across both the gap and the support piece 57. Specifically, the surface of the platen 24 includes an indentation 90 to fit the sealing membrane 86 such that it rests flush with the top surface of the platen 24. The polishing pad 30 is then mounted on top of the platen and sealing membrane combination. In the case of a two part polishing pad, the backing pad 34 is adhered to the platen 24 and sealing membrane 86 combination. The sealing membrane 86 is also adhered to the top surface of the support piece 57 and to the polishing pad segment 59, e.g., by an adhesive, such as a pressure sensitive adhesive (PSA).

Referring to FIG. 6C, the combination of the polishing pad segment 59 and the second sealing membrane 86 can be sold as a preassembled unit. Specifically, the polishing pad segment 59 can be attached, e.g., with a pressure sensitive adhesive, to the center of the flexible sealing membrane 86, e.g., a silicone or latex membrane, so that the edges of the sealing membrane 86 extend beyond the edges of the polishing pad segment. In addition, the lower surface 92 and the outer rim of the upper surface 93 of the sealing membrane can be coated with adhesive layers 94, and each adhesive layer can be covered by a liner 95.

During installation, the liner 95 is removed from the lower surface 92 of the membrane 86, and the unit is adhered to the top of the support piece 57 and to the indentation 90 of the platen 24. The top surface of the membrane 86 can be generally co-planar with the top surface of the platen 24. The liner 95 can be removed from the top surface of the membrane, and a polishing pad 30 can be secured to the top surface of the platen so that the aperture 33 fits around the polishing pad segment 59 and the edge of the membrane adjacent the aperture rests on the rim of the upper surface 93 of the membrane 86.

FIG. 6D illustrates a system in which the strain sensor 46 is mounted within an inset piece 100 that is seated within the recess 26 of the platen 24. A sealing membrane 102 can then be mounted between the inset piece 100 and the substrate contacting member 58 instead of connecting the sealing membrane 102 to the platen 24. The sealing membrane 102 can be adhered or fastened between the contacts support piece and the inset piece 100 in the same manner as described in FIGS. 6A-6B. Use of the inset piece 100 can allow for a modular piece that can be seated into the platen 24 without having to then secure the sealing membrane 102 to the platen 24. The polishing pad 30 can then be adhered to the platen 24 and to the inset piece 100 after inset piece 100 has been placed within the recess.

Alternatively, polishing articles can be used in which the substrate contact member and seal are secured to the polishing pad such that the pad, seal, and substrate contact member can be removed from the platen as a single part. FIGS. 6E and 6F illustrate a method of making a polishing pad in which the seal and substrate contact member are integrated into the polishing pad. The method includes sealing the substrate contact member 58 to the pad by dispensing a sealing material into a mold 315. The mold 315 is flat, and made of a suitable material such that the sealing material 310 does not permanently adhere to the mold. In one implementation, a portion of the surface of the mold 315 features a raised rim 319. The rim 319 encloses a rimmed area 318. The rimmed area 318 is the same shape as the substrate contacting member, and is sized to fit the substrate contacting member.

The substrate contact member 58 is placed in the mold 315 to rest in the rimmed area 318. The polishing pad 30 may then be placed in the mold 315 so that an aperture 307 in the polishing pad fits around the rim 318 and the polishing pad 30 surrounds the substrate contact member 58. In one implementation, the polishing pad can be intrinsically formed with an aperture suitable for the later placement of the contact member. In another implementation, the aperture is cut into the polishing pad piece. The rimmed area 318 forms the bottom of a recess between the substrate contact member 58 and the polishing pad 30.

In one embodiment, an alignment fixture 305 having an outwardly extending projection 307 may be attached to the substrate contact member 58. The end of the alignment fixture opposite the outwardly extending projection 307 is secured to a side of the substrate contact member opposite the surface that makes contact with the substrate. The alignment fixture 305 is secured to the substrate contact member, e.g., by a glue or pressure sensitive adhesive. In one implementation, the alignment fixture can have a lip 311 that partially or completely surrounds the substrate contact member. The outwardly extending projection can be shaped as a circular or elliptical rod, a rectangular or square bar, or a cone.

As shown in FIG. 6M, when the pad is installed on the platen 24, the projection 307 of the alignment fixture 305 can be inserted into a receiving recess of an alignment receptacle 309. In this manner, the alignment fixture 305 and the substrate contact member 58 are mechanically coupled to the strain sensor 46, while permitting the pad and contact member 58 to be easily installed and removed as a unit. The alignment receptacle 309 also facilitates installation of the substrate contact member 58 and polishing pad 30 because an operator installing the pad can determine when the substrate contact member is properly positioned on the platen.

Sealing material 310 is then placed inside the gap between the substrate contact member 58 and the polishing pad 30. Enough sealing material 310 is placed inside the gap so that the sealing material creates a seal between the polishing pad 30, the substrate contact member 58, and the alignment rod 305. The sealing material is sufficiently flexible, so that the substrate contact member 58 can move in response to the frictional coefficient of the substrate undergoing polishing. A suitable sealing material includes silicone, latex, or polyurethane.

FIG. 6F shows a polishing pad constructed using the above method. The sealing material 310 makes a complete seal between the substrate contact member 58, the polishing pad 30, and the alignment fixture 305. The top surface 45 of the contact member 58 can be co-planar with the top surface 31 of the polishing pad 30. As a result of the rimmed area of the mold, the sealing material 310 is slightly recessed below the top surface 45 and 31. In an implementation, the polishing pad can be formed around the substrate contact member and seal, e.g., by curing the liquid pad material.

As shown in FIG. 6M, when the pad is installed on the platen 24, the projection 307 of the alignment fixture 305 can be inserted into a receiving recess of an alignment receptacle 309. In this manner, the alignment fixture 305 and the substrate contact member 58 are mechanically coupled to the strain sensor 46, while permitting the pad and contact member 58 to be easily installed and removed as a unit. The alignment receptacle 309 also facilitates installation of the substrate contact member 58 and polishing pad 30 because an operator installing the pad can determine when the substrate contact member is properly positioned on the platen.

FIGS. 6G and 6H show a polishing pad that incorporates a gasket layer. The polishing pad 30 and substrate contacting member 58 each include at least two layers, a top layer 259 and a subpad 224. A gap is formed between the substrate contacting member 58 and the polishing pad 30. This gap permits the patch pad to move freely in response to frictional forces during the polishing operation. A gasket layer 284 located between the top layer 259 and the subpad 224 prevents liquid from passing through the gap area. FIG. 6G shows one implementation, in which the gasket layer 284 extends across substantially the entire polishing pad 30. FIG. 6H shows an alternative implementation, in which the gasket layer only extends across part of the polishing pad 30, specifically, the portion of the pad immediately adjacent the aperture 307. In both implementations, the gasket layer is only exposed in the patch region. The gasket layer is made of a material that is flexible and liquid-impermeable, e.g. silicone, latex, or polyurethane.

FIG. 6L shows a two-piece pad using a shroud sealing layer, where the shroud is incorporated into the polishing pad. In this implementation, the polishing pad 30 is intrinsically formed with an aperture to accommodate a substrate contacting member. During the polishing pad's formation process, a shroud 290 is inserted between the top layer 259 and a subpad 224. The shroud can extend through only part of the polishing pad, e.g. as shown in FIG. 6L, or can extend through the entire polishing pad (not shown). The shroud acts as a sealing layer, and is made from a material that is flexible and impervious to liquids, e.g. silicone, latex, or polyurethane. The polishing pad is attached to the platen 24, in the manner described above. The substrate contacting member 58 is then secured to the shroud 290 using a suitable means, e.g. pressure sensitive adhesive.

In one implementation, the substrate contacting member 58 can have an alignment rod 292 attached to it, in which case the alignment rod is inserted through an aperture in the shroud 290, so that the alignment rod extends through the shroud, and the substrate contacting member 58 can be secured as described above.

FIG. 6I shows a polishing pad that incorporates an O-ring 286 in lieu of the gasket layer to seal the space between the polishing pad 30 and the substrate contacting member 58. The O-ring can be secured to the polishing pad 30 and the substrate contacting member 58 by an adhesive material or by the compressive force exerted on the O-ring by the polishing pad 30 and the substrate contacting member 58.

FIG. 6J shows a polishing pad in which the substrate contacting member is formed as an integral part of the polishing layer. The polishing pad 30 can include two layers, a top layer 259 and a subpad 224, although the concept would be applicable to a single-layer pad. In one implementation, a substrate contacting member 58 is formed within the polishing pad by milling the polishing pad 30 to create a series of notches 274, 276 in the region where the substrate contacting member is desired. The notches 274, 276 are positioned such that the portion of the polishing pad within the notched area is the substrate contacting member. The notches form a flexure 273 that mechanically decouples the substrate contacting member 58 from the polishing pad 30, allowing the substrate contacting member to move sufficiently in response to frictional forces during the polishing operation to permit the detection of the frictional coefficient. The notches 274 should not extend beyond the top layer 259 into the subpad 224, as the subpad 224 is not impermeable to liquids. In an alternative implementation, the top layer with the flexure that forms the substrate contacting member is preformed in a mold so that the notches are created during the molding process. In either implementation, no additional sealing material is required, as the polishing layer and substrate contacting member are made from one continuous piece of material impervious to liquids, without having any openings for the polishing slurry to pass through.

FIG. 6K shows a two-piece pad using a shroud sealing layer, where the shroud is attached to the substrate contacting member. A shroud 290 is attached to the substrate contacting member 58. The shroud acts as a sealing layer, and is made from a material that is flexible and impervious to liquids, e.g. silicone, latex, or polyurethane. In one implementation, the patch is connected to an alignment rod 292. The shroud 290 extends beyond the edge of the substrate contacting member 58, and rests on the platen 24. A recess 355 can be formed in the platen 24, e.g. by machining, in order to accommodate the shroud 290 without causing the deformation of the polishing pad 30. The polishing pad 30, with an aperture to accommodate the substrate contacting member, may then be placed on the platen 24, thereby securing the shroud 290. In an alternative implementation, the polishing pad 30 may be formed around the substrate contacting member 58, e.g., by curing the liquid pad material while it is in contact with the shroud.

Referring to FIG. 7A, substrate 10 can include a silicon wafer 12 and one or more deposited layers 14 and 16. The deposited layers can be semiconductor, conductor, or insulating layers. After a layer has been deposited, a pattern can be etched, for example, using photolithographic techniques. Subsequent layers can then be deposited over the pattered layer. As shown in FIGS. 7A-7C, substrate 10 can be polished to reduce the thickness of deposited layer 16 until the patterned layer 14 is exposed and the top surfaces of layers 14 and 16 are co-planar. Alternatively, substrate 10 can be polished until deposited layer 16 is planarized.

Different substrate layers have different coefficients of friction between the deposited layers and the strain sensor 46. This difference in coefficients of friction means that different deposited layers will generate different amounts of frictional force, and thus different amounts of strain in the leaf spring 48. If the coefficient of friction increases, the deformation of the leaf spring 48 will increase. Similarly, if the coefficient of friction decreases, the deformation of the leaf spring 48 will decrease. When deposited layer 16 has been polished down to expose the patterned layer 14, the strain will change to reflect the different coefficient of friction between the material of the deposited layer 14 and the polishing pad 30. Consequently, a computing device, such as the computer 90, can be used to determine the polishing endpoint by monitoring the changes in strain, and thus friction, detected by the strain measuring device.

Referring now to FIGS. 8A and 8B, two exemplar graphs are shown illustrating possible changes in detected friction at different points during a polishing process. FIG. 8A is a graph of friction versus time during a hypothetical chemical mechanical polishing process in which the coefficient of friction for patterned layer 14 is less than the coefficient of friction for deposited layer 16. Similarly, FIG. 8B is a graph of friction versus time during a hypothetical polishing process in which the coefficient of friction for patterned layer 14 is greater than the coefficient of friction for deposited layer 16.

Referring to FIG. 7A, at the beginning of a polishing process, the surface of layer 16 may not be planar, but instead may have peaks and valleys resulting from the deposition process. A non-planar surface results in a higher friction then a planar surface for the same material; Thus, as shown in FIG. 8A, the initial non-planar surface is represented by high friction at the beginning of the graph.

Turning to FIG. 7B, the deposited layer 16 has been planarized, but patterned layer 14 has not yet been revealed. In FIG. 8A, this situation is illustrated by a change in the friction from a higher level to a lower level as a result of the decreased friction.

Finally, in FIG. 7C, the polishing process has reduced the thickness of deposited layer 16 to reveal the patterned layer 14. In this example, the patterned layer 14 has a lower coefficient of friction then the deposited layer 16. As a result, in FIG. 8A the graph shows that the friction has again decreased. The level of friction corresponds to the endpoint of the polishing process. As a result, the friction decreases throughout the polishing process.

Referring now to FIG. 8B, the initial non-planar surface is represented by high friction at the beginning of the graph, and planarization of the deposited layer 16 is illustrated by a change in the friction from a higher level to a lower level as a result of the decreased friction, for the planarized layer 16.

In this example, the underlying layer 14 has a higher coefficient of friction then the deposited layer 16. Thus, when the polishing process has reduced the thickness of deposited layer 16 to reveal the underlying layer 14, in FIG. 8B the graph shows that the friction has increased. The level of friction corresponds to the endpoint of the polishing process. As a result, the friction increases from the planarization point to the endpoint condition.

As mentioned above, FIGS. 8A and 8B are example graphs and the actual relative changes in the frictional force depend upon the materials being used for the deposited layers and the degree of initial roughness of deposited layer 16. Specific endpoint frictional values can be determined through experimentation.

The system can also be used to trigger a polishing endpoint based on the degree of planarization of the deposited layer 16 (rather than exposure of the underlying layer 14). In this implementation, the endpoint can be triggered by detection of the initial decrease in friction caused by planarization.

Referring now to FIGS. 2 and 9, a computer 90 can be used to control polishing station 22. The computer 90 can receive input from the strain gauges 50 and display the result on a monitor 92. Additionally, a computer program can be designed to control the starting and stopping of a chemical mechanical polishing process. As shown in FIG. 9, an implementation of a computer program for chemical mechanical polishing begins with the initiation of a chemical mechanical polishing process on the substrate 10 (step 910). During the polishing process, the computer 90 receives input from the strain gauges 50 (step 920). Input from the strain gauges 50 can be received continuously, periodically, or some combination of both. The computer 90 receives the strain input signal to determine the strain experienced by the strain gauges 50 (step 930). The computer 90 then monitors the signal for changes in strain (step 940). When the strain change indicates a desired polishing endpoint, the computer 90 ends the polishing process (step 950). In one implementation, the computer 90 detects changes in the slope of the strain data to determine a polishing endpoint. The computer 90 can also monitor for strain signal smoothing to determine a polishing endpoint. Alternatively, the computer 90 consults a database containing pre-determined endpoint strain values based on the deposited layers used in order to determine the occurrence of an endpoint.

In addition, the computer 90 can sort the measurements from the strain sensor 46 into radial ranges, as described for optical measurements in U.S. Pat. No. 6,159,073. The measurements may then be used for real-time closed loop control of the pressure applied by the carrier head 70. For example, if the computer 90 detects that the friction is changing in a radial zone at the edge of the substrate, this can indicate that the underlying layer is being exposed first at the edge of the substrate. In response, the computer 90 can cause the carrier head 70 to apply less pressure at the edges of the substrate than at the center.

A circuit schematic combining strain gauges 50 and amplifier 54 is shown in FIG. 10. In this example, the strain gauges 50 are represented as resistors RS1-RS4 each resistor having an unstrained resistance of 350 ohms. The strain gauges 50 are connected together such that RS1 and RS2 increase resistance when the spring leaf undergoes strain and strain gauges RS3 and RS4 decrease resistance when the spring leaf undergoes strain. The voltage across the strain gauges will vary depending on the amount of strain. The output voltage is used by the amplifier circuit shown in FIG. 10 to provide gain to the output signal from the strain gauges 50. The amount of gain depends, in part, upon the value of resistor RG For example, for the circuit shown in FIG. 10 resistor values between 500 ohms and 50 ohms can produce an approximate gain between 100 and 1000. The output of the amplifier can then be transmitted to a computer for processing.

The strain sensor 46 can be integrated into in a variety of polishing systems. During a polishing process, the substrate 10 and the polishing article move relative to one another. Assuming that the strain sensor 46 moves with the polishing article, then either the polishing article support, e.g., the platen 24, or the carrier head 70, or both can move to provide relative motion between the strain sensor 46 and the substrate 10. Alternatively, the strain sensor need not move with the polishing article. In this case, the strain sensor could be remain immobile and the carrier head 70 could move to provide relative motion between the strain sensor 46 and the substrate. The polishing article can be a circular (or some other shape) pad secured to a platen, a tape extending between supply and take-up rollers, or a continuous belt. The polishing article can be affixed on a platen, incrementally advanced over a platen between polishing operations, or driven continuously over the platen during polishing. The polishing article can be a standard (e.g. polyurethane with or without fillers) rough pad, a soft pad, or a fixed-abrasive pad. A suitable opening can be created in any of the aforementioned polishing pads 30 and positioned on a the platen 24 such that the strain sensor 46, having a contact surface 45 with a cross sectional area less than that of the substrate 10, can physically contact the substrate 10 during a chemical mechanical polishing process. The slurry 38 supplied to the polishing article can include abrasives or abrasive-free.

In one implementation, the polishing pad segment 59 is directly connected to the leaf spring 48 without the presence of the support piece 57. Additionally, in implementations without the support piece 57, the sealing membranes 84, 86, 88, and 102 can be attached directly to the leaf spring 48.

In another alternative implementation, the restorative material itself provides the substrate contacting member 58. For example, the restorative material can be a bendable sheet (having the same general shape as the leaf spring) formed of a material that does not scratch the substrate, such as a soft polyurethane. This bendable sheet can extend from the recess 26 such that its top surface, having a cross sectional area less than that of the substrate 10, rests co-planar to the polishing surface 31 when the polishing pad 30 is installed on platen 24. In addition, rather than a leaf spring, the restorative material can be a square or round metal rod.

The restorative material can be any material that exerts a force in opposition to its deformation by an external force, such as an elastic or compressible member. The restorative material can connect (optionally via an intermediate fixture, as shown in FIG. 6C) the substrate contacting member 58 to the polishing article support. For example, as shown in FIG. 11, the strain sensor 46 can include a plurality of springs 110 as the restorative material connecting the substrate contacting member 58 to the platen 24, allowing the member to move laterally under a frictional force caused by contact with the substrate 10. The displacement of the substrate contacting member 58, indicative of the strain experienced by the attached springs, can be monitored optically, e.g., by a laser interferometer 112, or by a capacitive or eddy sensor, or by other displacement measurement sensors. Alternatively, a light beam 120 can be directed from a light source 122 to reflect off the side of the substrate contacting member 58 and onto a position-sensitive light detector 124. The displacement of the substrate contacting member 58 causes the position at which the light beam impinges the detector 124 to change, thus providing a signal indicative of the lateral displacement of the member 58 and the frictional coefficient. Assuming that the strain sensor 46 does not move with the polishing article, the restorative material can connect the substrate contacting member 58 to an immobile fixture, such as the machine base 21 that supports the platens.

In still another alternative implementation illustrated in FIG. 12, the friction sensing system includes a strain sensor that is configured to slide laterally rather than bend under frictional force from the substrate. In this implementation, the friction sensor 246 includes a substrate contacting member 58 that can move when subjected to frictional force from the substrate 10, a generally rigid sliding rod 248 connected to the substrate contacting member 58, a spring 249 to urge the sliding rod 248 and substrate contacting member 58 back towards a neutral position, and a pressure sensor 250 that generates a signal based on the displacement of the substrate contacting member 58 and sliding rod 248.

The rod 248 is slidably attached to a base 254, which can be secured to or be part of the platen. The sliding rod 248 transmits the displacement of the substrate contacting member 58 to the pressure sensor 250. The motion of the sliding rod 248 can be limited by a channel 252 in base 254, so that the sliding rod 248 is restricted to travel along an axis parallel to the direction of relative motion between the substrate and the friction sensor 246.

Frictional forces on the substrate contacting member 58 will cause lateral displacement of both the substrate contacting member 58 and the sliding rod 248. This causes the sliding rod 248 to exert pressure against the pressure sensor 250, with greater pressure applied when the substrate contacting member 58 is subject to greater frictional forces. The pressure sensor can be coupled to an output system (not shown).

The spring 249 is mounted to the sliding rod 248. The spring 249 can be formed from a metallic material, such as stainless steel. The composition of the spring 249 can be chosen based on the expected frictional forces so that the spring compresses and extends elastically (without undergoing inelastic deformation) when the friction sensor 246 is subjected to a frictional force caused by contact with the substrate. The spring 249 is oriented so that the restorative force is parallel to the direction of relative motion between the substrate and the friction sensor 246. In this way, the spring 249 will exert a restorative force against the displacement of the sliding rod 248 and the substrate contacting member 58.

The substrate contacting member 58 is attached to the sliding rod 248 such that the substrate contacting member 58 is co-planar with the polishing pad 30. The substrate contacting member 58 can be a single piece or include other components, such as a support piece and a polishing pad segment, so that the resulting top surface of the friction sensor 246 is co-planar with the polishing pad 30. An advantage of this implementation is that the substrate contact member always remains parallel to the surface of the polishing pad and the substrate, and therefore the entire surface of the substrate contact member remains in contact with the substrate. This allows for a more accurate determination of the frictional force being exerted by the substrate on the substrate contact member.

The output of the pressure sensor 250 is sent to computer 90 for processing. Processing can include calculation of a frictional coefficient between the substrate contacting member 58 and the substrate 10, associating measurements from the friction sensor 246 with radial positions on the substrate 10, analyzing the progress of a chemical mechanical polishing process based on the pressure measurements, controlling the polishing apparatus based on changes in the measured pressure, and translating the pressure measurements into graphical information. An output can be displayed by a device such as a monitor 92.

In another embodiment, which can be combined with the various implementations discussed above, the friction sensing system includes multiple sensors. For example, as shown in FIG. 13A, the system can include multiple sensors placed at substantially the same distance from but at equal angular intervals around the axis of rotation of the platen. As another example, as shown in FIG. 13B, the system can include sensors placed in close proximity, but with different, e.g., perpendicular, orientations (e.g., one sensor to measure displacement of its substrate contact member parallel to a radius passing through the axis of rotation 25 of the platen, and another sensor to measure displacement of its substrate contact member perpendicular to a radius passing through the axis of rotation 25 of the platen). With this configuration, the system can generate a measurement indicative of a total frictional force, e.g., as a square root of the sum of the squares of the strains measured in the two perpendicular directions.

As still another example, the substrate contact member could be laterally movable both parallel and perpendicular to a radius passing through the axis of rotation 25 of the platen, and the friction sensing system can include sensors to measure displacement of the member along both directions. For example, referring to FIG. 14, instead of a leaf spring, the strain sensor can include a flexible support post 170 with a rectangular cross-section. A first set of strain sensors 50a can be located on one pair of opposing faces of the support post 170 to measure the flexing of the support post in one direction, and a second set of strain sensors 50b can be located on the other pair of opposing faces to measure the flexing of the support post in a perpendicular direction. Each set of strain sensors can be connected as discussed in reference to FIGS. 4A-5, thus generating measurements of the frictional force in two perpendicular directions. With this configuration, the system can generate a measurement indicative of a total frictional force on the substrate contact member, e.g., as a square root of the sum of the squares of the strains measured in the two perpendicular directions.

In any implementation, the computer 90 can perform processing steps on the received raw strain data in order to convert the data into frictional values. The computer 90 can use the relationship between the strain of the strain gauges 50 and the frictional force exerted on the substrate contacting member 58 to calculate the coefficient of friction. Endpoint determination can then be made based on coefficient of friction.

The polishing operation can be a polishing operation that removes a conductive, insulative or semiconductive layer to expose another layer of the same type, i.e., conductive, insulative or semiconductive. Alternatively, the polishing operation can be a polishing operation that removes that removes a conductive, insulative or semiconductive layer to expose another layer of a different type. In either case, the polishing operation can be a polishing operation that removes a layer to expose another layer having similar reflectivity, e.g., two insulative layers. For example, the layer being polished may be a nitride and the layer being exposed may be an oxide, or vice versa, or both layers may be oxides. The polishing operation can be a step in a shallow trench isolation (STI), inter-layer dielectric (ILD), inter-metallic dielectric (IMD) and pre-metal dielectric (PDM), polysilicon, or silicon on insulator (SOI) process.

The invention can be implemented with digital electronic circuitry, or with computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. The essential elements of a computer are a processor for executing instructions and a memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

The invention has been described in terms of particular implementations. Other implementations are within the scope of the following claims.

What is claimed is:

1. A polishing system, comprising:
   a movable platen;
   a polishing pad connected to the movable platen having a polishing surface and having an aperture therein;
   a substrate contacting member contained within the aperture having a top surface to contact an exposed surface of a substrate, wherein the top surface is substantially coplanar with the polishing surface;
   a sensor to measure a lateral displacement of the substrate contacting member and generate a signal based on the lateral displacement of the substrate; and
   a controller to receive the signal from the sensor.

2. The system of claim 1, wherein the sensor is a strain gauge.

3. The system of claim 1, wherein the sensor is a pressure gauge.

4. The system of claim 1, further comprising an alignment device coupled between the substrate contacting member and the sensor.

5. The system of claim 1, further comprising the polishing pad having a top surface to contact the exposed surface of the substrate, wherein the polishing pad surrounds, but does not contact, the substrate contacting member.

6. The system of claim 5, further comprising a sealing piece extending between the substrate contacting member and the polishing pad, wherein the sealing piece is made of a flexible, fluid-impermeable material.

7. The system of claim 6, wherein the sealing piece is made of silicone, latex, or polyurethane.

8. The system of claim 6, wherein the sealing piece is an O-ring.

9. The system of claim 8, wherein the O-ring is secured to the substrate contacting member and the polishing pad with an adhesive material.

10. The system of claim 6, wherein the sealing piece extends through the substrate contacting member.

11. The system of claim 1, further comprising:
    the polishing pad having a top surface to contact the exposed surface of the substrate, wherein the polishing pad is made from the same piece of material as the substrate contacting member; and
    a flexure, such that the flexure mechanically isolates the substrate contacting member from the polishing pad.

12. An article for use in a polishing system, comprising:
    a polishing pad having a polishing surface;
    a substrate contacting member having a top surface to contact an exposed surface of substrate, wherein the top surface is substantially coplanar with the polishing surface; and
    a seal formed of a flexible and fluid-impermeable material securing the substrate contacting member to the polishing pad and permitting the substrate contacting member to move laterally relative to the polishing pad.

13. The article of claim 12, wherein the polishing pad has two or more layers.

14. The article of claim 13, wherein the seal is secured between two layers of the polishing pad piece.

15. The article of claim 14, wherein the seal extends through the entire polishing pad piece.

16. The article of claim 14, wherein the seal extends only partially into the polishing pad piece.

17. The article of claim 12, further comprising an alignment device, wherein a first surface of the alignment device is attached to the substrate contacting member.

18. The article of claim 17, wherein the sealing material is also in contact with the alignment device.

19. The article of claim 17, wherein an alignment rod extends from a second surface of the alignment device.

20. The article of claim 12, wherein the top surface of the substrate contacting member is composed of the same material as the polishing pad.

21. The article of claim 12, wherein the top surface of the substrate contacting member includes grooves that channel liquid away from the substrate contacting member.

22. The article of claim 12, wherein the seal is an O-ring.

23. The article of claim 12, wherein the seal is comprised of latex, silicone, or polyurethane.

24. The article of claim 12, wherein the polishing pad and the substrate contacting member are manufactured from one continuous piece of material.

* * * * *